(12) United States Patent
Dravid et al.

(10) Patent No.: US 11,510,872 B2
(45) Date of Patent: Nov. 29, 2022

(54) NANOPARTICLE-LIPID COMPOSITE CARRIERS AND USES THEREOF

(71) Applicant: Northwestern University, Evanston, IL (US)

(72) Inventors: Vinayak P. Dravid, Glenview, IL (US); Vikas Nandwana, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/615,260

(22) PCT Filed: May 24, 2018

(86) PCT No.: PCT/US2018/034442
§ 371 (c)(1),
(2) Date: Nov. 20, 2019

(87) PCT Pub. No.: WO2018/218052
PCT Pub. Date: Nov. 29, 2018

(65) Prior Publication Data
US 2020/0170946 A1 Jun. 4, 2020

Related U.S. Application Data

(60) Provisional application No. 62/510,468, filed on May 24, 2017.

(51) Int. Cl.
| | | |
|---|---|---|
| *A61K 9/107* | (2006.01) | |
| *A61K 49/18* | (2006.01) | |
| *A61K 41/00* | (2020.01) | |
| *A61K 31/337* | (2006.01) | |
| *A61K 33/243* | (2019.01) | |

(52) U.S. Cl.
CPC ............ *A61K 9/107* (2013.01); *A61K 31/337* (2013.01); *A61K 33/243* (2019.01); *A61K 41/0028* (2013.01); *A61K 41/0052* (2013.01); *A61K 49/1809* (2013.01)

(58) Field of Classification Search
CPC ...... A61K 9/107; A61K 47/02; A61K 33/243; A61K 31/337
See application file for complete search history.

(56) References Cited

U.S. PATENT DOCUMENTS

| | | | |
|---|---|---|---|
| 8,945,628 B2 | 2/2015 | Weissleder et al. | |
| 2003/0082237 A1 | 5/2003 | Cha et al. | |
| 2003/0203865 A1 | 10/2003 | Harvie et al. | |
| 2005/0158390 A1* | 7/2005 | Rana ...................... | B82Y 30/00 424/489 |
| 2007/0116753 A1* | 5/2007 | Hong .................... | A61K 31/337 424/450 |
| 2013/0243848 A1* | 9/2013 | Lobovkina ........... | A61K 47/543 424/490 |
| 2013/0315831 A1* | 11/2013 | Shi ....................... | A61K 9/5073 424/9.1 |
| 2015/0182461 A1 | 7/2015 | Kim | |
| 2015/0231282 A1 | 8/2015 | Pozzo et al. | |
| 2017/0367982 A1 | 12/2017 | Nandwana et al. | |
| 2019/0091154 A1 | 3/2019 | Nandwana et al. | |
| 2020/0101177 A1 | 4/2020 | Nandwana et al. | |

OTHER PUBLICATIONS

Anupama Bhat et al., Effects of gold nanoparticles on lipid packing and membrane pore formation, Appl. Phys.Lett, 109, 263106. (Year: 2016).*
Yang et al., Drug Delivery Using Nanoparticle-Stabilized Nanocapsules, Angew. Chemie, 123, 497-503 (Year: 2011).*
Geoffrey D. Bothun et al., Cationic Gel-Phase Liposomes with "Decorated" Anionic SPIO Nanoparticles: Morphology, Colloidal, and Bilayer Properties, Langmuir, 27, 8654-8652 (Year: 2011).*
Elham Cheraghipour et al., Citrate capped superparamagnetic iron oxide nanoparticles used for hyperthermia therapy, J. Biomedical Science and Engineering, 5, 715-719 (Year: 2012).*
Kunn Hadinoto et al., Lipid-polymer hybrid nanoparticles as a new generation therapeutic delivery platform: A review, European J of Pharmaceutics and Biopharmaceutics, 85, 427-443. (Year: 2013).*
The International Search Report and Written Opinion issued in International Patent Application No. PCT/US18/34442 dated Aug. 23, 2018, pp. 1-9.
Yang, Xiao-Chao, et al. "Drug Delivery Using Nanoparticle-Stabilized Nanocapsules," *Angewandte Chemie International Edition* 50.2 (2011): 477-481.
Tao, Youhua, et al. "Reduction-responsive gold-nanoparticle-conjugated Pluronic micelles: an effective anti-cancer drug delivery system." *Journal of Materials Chemistry* 22.36 (2012): 18864-18871.
Bica et al., Sterically stabilized water based magnetic fluids: Synthesis, structure and properties. Journal of Magnetism and Magnetic Materials Apr. 2007; 311(1):17-21.
Cormode et al., Atherosclerotic plaque composition: analysis with multicolor CT and targeted gold nanoparticles. Radiology. Sep. 2010;256(3):774-82.
Cormode et al., Nanocrystal core high-density lipoproteins: a multimodality contrast agent platform. Nano Lett. Nov. 2008;8(11):3715-23.
Damiano et al., Templated high density lipoprotein nanoparticles as potential therapies and for molecular delivery. Adv Drug Deliv Rev. May 2013;65(5):649-62.
Fay et al., Nanocrystal Core Lipoprotein Biomimetics for Imaging of Lipoproteins and Associated Diseases. Curr Cardiovasc Imaging Rep. Feb. 1, 2013;6(1):45-54.

(Continued)

*Primary Examiner* — Michael G. Hartley
*Assistant Examiner* — Jagadishwar R Samala
(74) *Attorney, Agent, or Firm* — Bell & Manning, LLC

(57) ABSTRACT

Provided herein are nanoparticle-lipid composite carriers as theranostic agents, particularly for diagnosis and/or treatment of cancers and related diseases and conditions. In particular embodiments, the carrier composites comprise a lipid core and an outer shell of functionalized nanoparticles (fNPs).

18 Claims, 16 Drawing Sheets

(56) References Cited

OTHER PUBLICATIONS

Fayad et al., Recombinant HDL-like nanoparticles: a specific contrast agent for MRI of atherosclerotic plaques. J Am Chem Soc. Dec. 22, 2004;126(50):16316-7.

Fournier et al., HDL phospholipid content and composition as a major factor determining cholesterol efflux capacity from Fu5AH cells to human serum. Arterioscler Thromb Vasc Biol. Nov. 1997;17(11):2685-91.

Frias et al., Properties of a versatile nanoparticle platform contrast agent to image and characterize atherosclerotic plaques by magnetic resonance imaging. Nano Lett. Oct. 2006;6(10):2220-4.

Frullano et al., Multimodal MRI contrast agents. J Biol Inorg Chem. Sep. 2007;12(7):939-49.

Hung et al., Mechanisms of Gadographene-Mediated Proton Spin Relaxation. J Phys Chem C. 2013;117(31):16263-73.

Ingram et al., Superparamagnetic nanoclusters coated witn oieic acid biiayers tor stabilization of emulsions of water and oil at low concentration. J Colloid Interface Sci. Nov. 1, 2010;351(1):225-32.

Lan et al., Synthesis of bilayer oleic acid-coated Fe3O4 nanoparticles and their application in pH-responsive Pickering emulsions. J Colloid Interface Sci. Jun. 1, 2007;310(1):260-9.

Marrache et al., Biodegradable synthetic high-density lipoprotein nanoparticles for atherosclerosis. Proc Natl Acad Sci U S A. Jun. 4, 2013;110(23):9445-50.

Matosziuk et al., Structural optimization of Zn(II)-activated magnetic resonance imaging probes. Inorg Chem. Nov. 4, 2013;52(21):12250-61.

Skajaa et al., The biological properties of iron oxide core high-density lipoprotein in experimental atherosclerosis. Biomaterials. Jan. 2011;32(1):206-13.

Thaxton et al., Templated spherical high density lipoprotein nanoparticles. J Am Chem Soc. Feb. 4, 2009;131(4):1384-5.

Yetukuri et al., Composition and lipid spatial distribution of HDL particles in subjects with low and high HDL-cholesterol. J Lipid Res. Aug. 2010;51(8):2341-51.

Xie et al., "Enhanced Soft Magnetic Properties of Iron-Based Powder Cores with Co-Existence of Fe3O4—MnZnFe2O4 Nanoparticles," Metals, 2018, vol. 8, 702. pp. 1-11.

Nandwana et al., "Engineered Theranostic Magnetic Nanostructures: Role of Composition and Surface Coating on Magnetic Resonance Imaging Contrast and Thermal Activation," ACS Appl. Mater. Interfaces, 2016, vol. 8, pp. 6953-6961.

Nandwana et al., "High-Density Lipoprotein-like Magnetic Nanostructures (HDL-MNS): Theranostic Agents for Cardiovascular Disease," Chem. Mater., 2017, vol. 29, pp. 2276-2282.

Lee et al., "Artificially engineered magnetic nanoparticles for ultra-sensitive molecular imaging," Nature Medicine, Jan. 2007, vol. 13, No. 1, pp. 95-99.

Jang et al., "Critical Enhancements of MRI Contrast and Hyperthermic Effects by Dopant-Controlled Magnetic Nanoparticles**," Angew. Chem., 2009, vol. 121, pp. 1260-1264.

Zhang et al., "Detection and Treatment of Atherosclerosis Using Nanoparticles," Wiley Interdiscip rev Nanomed Nanobiotechnol. Jan. 2017: 9(1): Doi:10.1002/wnan.1412, pp. 1-39.

R.Y. Hong et al., "On the Fe3O4/Mn1—xZnxFe2O4 core/shell magnetic nanoparticles," *Journal of Alloys and Compounds* (2009), vol. 480; pp. 947-953.

A.S. Nikolic et al., "Magnetite/Mn-ferrite nanocomposite with improved magnetic properties," *Materials Letters* (2014), vol. 120; pp. 86-89.

Sreekanth Perumbilavil et al., "Enhanced Ultrafast Nonlinear Optical Response in Ferrite Core/Shell Nanostructures with Excellent Optical Limiting Performance," *Small* 2018, vol. 14; pp. 1701001 (1 of 9).

* cited by examiner

NANOPARTICLE-LIPID COMPOSITE CARRIERS AND USES THEREOF

CROSS-REFERENCE TO RELATED APPLICATION

This application is a National Stage of International Application No. PCT/US18/34442, filed May 24, 2018, which claims the benefit of U.S. Patent Application No. 62/510,468, filed May 24, 2017, the contents of each of which are herein incorporated by reference in its entirety.

FIELD OF THE INVENTION

Provided herein are nanoparticle-lipid composite carriers as theranostic agents, particularly for diagnosis and/or treatment of cancers and related diseases and conditions. In particular embodiments, the carrier composites comprise a lipid core and an outer shell of functionalized nanoparticles (fNPs).

BACKGROUND OF THE INVENTION

Magnetic nanostructures (MNS) have received significant attention due to their ability to enhance localized contrast in magnetic resonance imaging (MRI) and heat under external radio frequency (RF) field, respectively (Ref 3; incorporated by reference in its entirety). A typical MNS is composed of magnetic nanoparticle as core and hydrophilic shell. While the core provides theranostic properties, the shell provides stability, biocompatibility, and a surface amenable to functionalize targeting agents (Ref 4; incorporated by reference in its entirety).

While MNSs as T2 MRI contrast agents have been well established in diagnostic imaging (Ref 4c; incorporated by reference in its entirety). A variety of nanocarrier platforms, such as silica, polymer, lipid, and hydrogel for targeted drug delivery with MNSs or other nanoparticles, have been reported (Ref 6; incorporated by reference in its entirety). In particular, lipid-based nanocarriers (liposomes, micelles, solid lipid nanoparticles, lipid nanocapsules) have evolved a multifunctional therapy platform due to excellent biocompatibility and biodegradability (Refs. 1b, 5a, 7; incorporated by reference in their entireties). In addition, the ability to entrap both hydrophilic and lipophilic drugs and protection of drugs from the surrounding environment gives them edge over other platforms. Their size, charge, and functionality can be modified via tuning their lipid concentration and surface chemistry (Ref 8; incorporated by reference in its entirety). Thirteen formulations of liposomes and lipid nanoparticles are approved as a therapeutic nanocarriers including first FDA approved nanomedicine, DOXIL (Ref 9; incorporated by reference in its entirety). However, lipid-based carriers pose several challenges, such as instability of the carrier, low capacity to load lipophilic drugs, and lack of controlled-release of encapsulated drugs (Ref 10; incorporated by reference in its entirety).

SUMMARY OF THE INVENTION

Provided herein are nanoparticle-lipid composite carriers as theranostic agents, particularly for diagnosis and/or treatment of cancers and related diseases and conditions. In particular embodiments, the carrier composites comprise a lipid core and an outer shell of functionalized nanoparticles (fNPs). In more particular embodiments, the outer shell comprises magnetic (e.g., $Fe_3O_4$), plasmonic (e.g., Au), semiconducting (e.g., ZnS quantum dot), and/or other detectable nanostructures, functionalized (e.g., with citrate or other negatively charged moiety) to facilitate interaction with the lipid (e.g., cationic lipid core).

In some embodiments, provided herein are nanoparticle-lipid composite carriers composed of functionalized nanopaticles (e.g., magnetic nanostructures, plasmonic nanostructures, quantum nanostructures, etc.) and lipids. While the hydrophobic core allows drug loading in a controlled manner, the fNP shell contributes enhanced detection properties (e.g., magnetic resonance contrast) and/or actuates drug release (e.g., under RF field). Additionally, the hydrophobic core is useful for containment of, and maximizing capacity for, hydrophobic cargo. In particular embodiments, nanoparticle-lipid composite carriers comprise a composite of magnetic nanostructures (outer shell) and a lipid core. Experiments conducted during development of embodiments herein demonstrate that when internalized into, for example, HEPG2 cells, MNS-lipid composite carriers (MLCCs) provide MR imaging functionality, and that drug release from MNS-lipid composite carriers causes cell death up to 75%. When coupled with desired targeting agents, MNS-lipid composite carriers find use in targeted therapeutic, diagnostic, research, and theranostic applications. The ability to diagnose, and treat at the same time and/or with the same agent makes magnetic-lipid composite nanoparticles a useful theranostic platform in biomedicine.

In some embodiments, provided herein MNS-lipid composite carriers, comprising: a hydrophobic core comprising a plurality of lipid tails and a shell comprising MNSs assembled on a plurality of lipid heads. In some embodiments, the MNSs are functionalized with a negatively charged moiety (e.g., citrate). In some embodiments, the negatively charged moiety is a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the lipid is a cationic lipid. In some embodiments, the lipid is an amphiphilic surfactants (e.g., comprising one or more hydrocarbon or fluorocarbon tails) and amphiphilic polymers with cationic head group (e.g., Cetrimonium bromide (CTAB), Cetylpyridinium chloride (CPC), Benzalkonium chloride (BAC), Benzethonium chloride (BZT), Dimethyldioctadecylammonium chloride, Dioctadecyldimethylammonium bromide (DODAB), etc.). In some embodiments, the lipid is a cationic lipid selected from DOTMA (1,2-di-O-octadecenyl-3-trimethylammonium propane (chloride salt)), DOBAQ (N-(4-carboxybenzyl)-N,N-dimethyl-2,3-bis(oleoyloxy)propan-1-aminium), 14:0 DAP (1,2-dimyristoyl-3-dimethylammonium-propane), 16:0 DAP (1,2-dipalmitoyl-3-dimethylammonium-propane), 18:0 DAP (1,2-distearoyl-3-dimethylammonium-propane), DODAP (1,2-dioleoyl-3-dimethylammonium-propane), DORIE (1,2-dioleyloxypropyl-3-dimethyl-hydroxyethylammonium bromide), DMRIE (1,2-dimyristyloxypropyl-3-dimethyl-hydroxyethylammonium bromide), GAP-DLRIE ((±+)-N-(3-aminopropyl)-N,N-dimethyl-2,3-bis(dodecyloxy)-1-propanaminium bromide), diC14-amidine (N-t-butyl-N'-tetradecyl-3-tetradecylaminopropionamidine), DOGS (Di-octadecyl-amido-glycyl-spermine), DOSPA ((+)-N,N-dimethyl-N-[2-(sperminecar-boxamido)ethyl]-2, 3-bis(dioleyloxy)-1-propaniminium pentahy-drochloride), DC-Cholesterol.HCl (3β-[N-(N',N'-dimethylaminoethane)-carbamoyl]cholesterol hydrochloride), GL67 (N4-Cholesteryl-Spermine HCL salt), BGTC (bis (guanidinium)-trencholesterol), MVL5 (N1-[2-((1S)-1-[(3-aminopropyl) amino]-4-[di(3-amino-propyl)amino]butylcarboxamido) ethyl]-3,4-di[oleyloxy]-benzamide), 12:0 EPC (Cl Salt) (1,2-dilauroyl-sn-glycero-3-ethylphosphocholine (chloride salt)), 14:0 EPC (Cl Salt) (1,2-dimyristoyl-sn-glycero-3-ethylphosphocholine (chloride salt)), 16:0 EPC (Cl Salt) (1,2-dipalmitoyl-sn-glycero-3-ethylphosphocholine (chloride salt)), 18:0 EPC (Cl Salt) (1,2-distearoyl-sn-glycero-3-ethylphosphocholine (chloride salt)), 18:1 EPC (Cl Salt) (1,2-dioleoyl-sn-glycero-3-ethylphosphocholine (chloride salt)), 16:0-18:1 EPC (Cl Salt) (1-palmitoyl-2-oleoyl-sn-glycero-3-ethylphosphocholine (chloride salt)), and 14:1 EPC (Tf Salt) (1,2-dimyristoleoyl-sn-glycero-3-ethylphosphocholine (Tf salt)). In some embodiments, the lipid is dimethyl dioctadecyl ammonium bromide (DDAB) or 1,2-dioleoyl-3-trimethylammonium-propane (DOTAP). In some embodiments, the magnetic-lipid composite nanoparticles encapsulate an active agent (e.g., a drug such as a chemotherapy agent). In some embodiments, the MNS is a magnetic nanoparticle. In some embodiments, an MNS has a diameter of 2-20 nm (e.g., 2, 4, 6, 8, 10, 12, 14, 16, 18, 20, or ranges therebetween). In some embodiments, a MNS-lipid composite carrier has a diameter of 100-1000 nm (e.g., 100, 150, 200, 250, 300, 350, 400, 450, 500, 550, 600, 650, 700, 750, 800, 850, 900, 950, 1000, or ranges therebetween). In some embodiments, the MNS-lipid composite carriers comprise MNSs of at least two different sizes. In some embodiments, MNSs comprise a magnetic core material comprising, for example, $MFe_2O_4$, wherein M is Fe, Mn, $Zn_{0.2}Mn_{0.8}$, etc. In some embodiments, the MNSs comprise a hydrophilic surface layer. In some embodiments, MNSs comprise a core material selected from FeCo, FePt, CoPt, Co, Ni, Fe, FeO, MFe2O4 (M=Co, Ni, Zn, CoxMn1-x, ZnxMn1-x, CoxZn1-x), MnO, Mn3O4, Co3O4

In some embodiments, provided herein are NP-lipid composite carriers comprising a shell of plasmonic nanostructures (PNS). In some embodiments, the PNS is a plasmonic nanoparticle (e.g., Au NP, Ag NP, Pt NP, Pd NP, or combinations thereof (e.g., Au/Ag NP, Pt/Pd NP, etc.) with a functionalized surface. In some embodiments, a PNS-lipid composite carrier comprises Au core NPs that are surface functionalized with a hydrophilic surface layer (e.g., a negatively-charged moiety, citrate, etc.). In some embodiments, the hydrophilic surface layer comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the hydrophilic surface layer comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the PNS is 2-20 nm (e.g., 2, 4, 6, 8, 10, 12, 14, 16, 18, 20, or ranges therebetween). In some embodiments, provided herein PNS-lipid composite carriers (PLCCs), comprising: a hydrophobic core comprising a plurality of lipid tails and a shell comprising PNSs assembled on a plurality of lipid heads. In some embodiments, the PNSs are functionalized with a negatively charged moiety (e.g., citrate). In some embodiments, the negatively charged moiety comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the lipid is a cationic lipid. In some embodiments, the lipid is an amphiphilic surfactants (e.g., comprising one or more hydrocarbon or fluorocarbon tails) and amphiphilic polymers with cationic head group (e.g., Cetrimonium bromide (CTAB), Cetylpyridinium chloride (CPC), Benzalkonium chloride (BAC), Benzethonium chloride (BZT), Dimethyldioctadecylammonium chloride, Dioctadecyldimethylammonium bromide (DODAB), etc.). In some embodiments, the lipid is a cationic lipid selected from DOTMA (1,2-di-O-octadecenyl-3-trimethylammonium propane (chloride salt)), DOBAQ (N-(4-carboxybenzyl)-N,N-dimethyl-2,3-bis(oleoyloxy)propan-1-aminium), 14:0 DAP (1,2-dimyristoyl-3-dimethylammonium-propane), 16:0 DAP (1,2-dipalmitoyl-3-dimethylammonium-propane), 18:0 DAP (1,2-distearoyl-3-dimethylammonium-propane), DODAP (1,2-dioleoyl-3-dimethylammonium-propane), DORIE (1,2-dioleyloxypropyl-3-dimethyl-hydroxyethylammonium bromide), DMRIE (1,2-dimyristyloxypropyl-3-dimethyl-hydroxyethylammonium bromide), GAP-DLRIE ((±+)-N-(3-aminopropyl)-N,N-dimethyl-2,3-bis(dodecyloxy)-1-propanaminium bromide), diC14-amidine (N-t-butyl-N'-tetradecyl-3-tetradecylaminopropionamidine), DOGS (Dioctadecyl-amido-glycyl-spermine), DOSPA ((+)-N,N-dimethyl-N-[2-(sperminecar-boxamido)ethyl]-2,3-bis (dioleyloxy)-1-propaniminium pentahy-drochloride), DC-Cholesterol.HCl (3β[N-(N', N'-dimethylaminoethane)-carbamoyl]cholesterol hydrochloride), GL67 (N4-Cholesteryl-Spermine HCL salt), BGTC (bis (guanidinium)-trencholesterol), MVL5 (N1-[2-((1S)-1-[(3-aminopropyl) amino]-4-[di(3-amino-propyl)amino]butylcarboxamido) ethyl]-3,4-di[oleyloxy]-benzamide), 12:0 EPC (Cl Salt) (1,2-dilauroyl-sn-glycero-3-ethylphosphocholine (chloride salt)), 14:0 EPC (Cl Salt) (1,2-dimyristoyl-sn-glycero-3-ethylphosphocholine (chloride salt)), 16:0 EPC (Cl Salt) (1,2-dipalmitoyl-sn-glycero-3-ethylphosphocholine (chloride salt)), 18:0 EPC (Cl Salt) (1,2-distearoyl-sn-glycero-3-ethylphosphocholine (chloride salt)), 18:1 EPC (Cl Salt) (1,2-dioleoyl-sn-glycero-3-ethylphosphocholine (chloride salt)), 16:0-18:1 EPC (Cl Salt) (1-palmitoyl-2-oleoyl-sn-glycero-3-ethylphosphocholine (chloride salt)), and 14:1 EPC (Tf Salt) (1,2-dimyristoleoyl-sn-glycero-3-ethylphosphocholine (Tf salt)). In some embodiments, the lipid is dimethyl dioctadecyl ammonium bromide (DDAB) or 1,2-dioleoyl-3-trimethylammonium-propane (DOTAP). In some embodiments, the PNS-lipid composite carrier encapsulates an active agent (e.g., a drug such as a chemotherapy agent). In some embodiments, a PNS-lipid composite carrier has a diameter of 100-1000 nm (e.g., 100, 150, 200, 250, 300, 350, 400, 450, 500, 550, 600, 650, 700, 750, 800, 850, 900, 950, 1000, or ranges therebetween). In some embodiments, the PNS-lipid composite carrier comprises PNSs of at least two different sizes. In some embodiments, PNSs comprise a plasmonic core material comprising, for example, Au, Ag, Pt, Pd, etc. In some embodiments, PNSs comprise a hydrophilic surface layer.

In some embodiments, provided herein are NP-lipid composite carriers comprising a shell of quantum (e.g., semiconducting) nanostructures (QNS). In some embodiments, the QNS is a ZnS nanoparticle or quantum dot with a functionalized surface. In some embodiments, a QNS-lipid composite carrier (QLCC) comprises ZnS core that is surface functionalized with a hydrophilic surface layer (e.g., a negatively-charged moiety, citrate, etc.). In some embodiments, the hydrophilic surface layer comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the core comprises one or more materials selected from the group including, but not limited to Ge, InN, InGaN, Si, InP, AlAs, InAs, AlGaN, CdSe, CdS, CdTe, PbSe, PbS, PbTe, ZnSe, ZnBeSe, ZnS, ZnBeS, GaSb, InSb, SiC, and GaN. In some embodiments, the QNS is 2-20 nm (e.g., 2, 4, 6, 8, 10, 12, 14, 16, 18, 20, or ranges therebetween). In some embodiments, provided herein are QNS-lipid composite carriers comprising: a hydrophobic core comprising a plurality of lipid tails and a shell comprising QNSs assembled on a plurality of lipid heads. In some embodiments, the QNSs are functionalized with a negatively charged moiety (e.g., citrate). In some embodiments, the negatively charged moiety comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the lipid is a cationic lipid. In some embodiments, the lipid is an amphiphilic surfactants (e.g., comprising one or more hydrocarbon or fluorocarbon tails) and amphiphilic polymers with cationic head group (e.g., Cetrimonium bromide (CTAB), Cetylpyridinium chloride (CPC), Benzalkonium chloride (BAC), Benzethonium chloride (BZT), Dimethyldioctadecylammonium chloride, Dioctadecyldimethylammonium bromide (DODAB), etc.). In some embodiments, the lipid is a cationic lipid selected from DOTMA (1,2-di-O-octadecenyl-3-trimethylammonium propane (chloride salt)), DOBAQ (N-(4-carboxybenzyl)-N,N-dimethyl-2,3-bis(oleoyloxy)propan-1-aminium), 14:0 DAP (1,2-dimyristoyl-3-dimethylammonium-propane), 16:0 DAP (1,2-dipalmitoyl-3-dimethylammonium-propane), 18:0 DAP (1,2-distearoyl-3-dimethylammonium-propane), DODAP (1,2-dioleoyl-3-dimethylammonium-propane), DORIE (1,2-dioleyloxypropyl-3-dimethyl-hydroxyethylammonium bromide), DMRIE (1,2-dimyristyloxypropyl-3-dimethyl-hydroxyethylammonium bromide), GAP-DLRIE ((±+)-N-(3-aminopropyl)-N,N-dimethyl-2,3-bis(dodecyloxy)-1-propanaminium bromide), diC14-amidine (N-t-butyl-N'-tetradecyl-3-tetradecylaminopropionamidine), DOGS (Di-octadecyl-amido-glycyl-spermine), DOSPA ((+)-N,N-dimethyl-N-[2-(sperminecar-boxamido)ethyl]-2,3-bis(dioleyloxy)-1-propaniminium pentahy-drochloride), DC-Cholesterol.HCl (3β-[N-(N-N'-dimethylaminoethane)-carbamoyl]cholesterol hydrochloride), GL67 (N4-Cholesteryl-Spermine HCL salt), BGTC (bis (guanidinium)-tren-cholesterol), MVL5 (N1-[2-((1S)-1-[(3-aminopropyl)amino]-4-[di(3-amino-propyl)amino]butylcarboxamido)ethyl]-3,4-di[oleyloxy]-benzamide), 12:0 EPC (Cl Salt) (1,2-dilauroyl-sn-glycero-3-ethylphosphocholine (chloride salt)), 14:0 EPC (Cl Salt) (1,2-dimyristoyl-sn-glycero-3-ethylphosphocholine (chloride salt)), 16:0 EPC (Cl Salt) (1,2-dipalmitoyl-sn-glycero-3-ethylphosphocholine (chloride salt)), 18:0 EPC (Cl Salt) (1,2-distearoyl-sn-glycero-3-ethylphosphocholine (chloride salt)), 18:1 EPC (Cl Salt) (1,2-dioleoyl-sn-glycero-3-ethylphosphocholine (chloride salt)), 16:0-18:1 EPC (Cl Salt) (1-palmitoyl-2-oleoyl-sn-glycero-3-ethylphosphocholine (chloride salt)), and 14:1 EPC (Tf Salt) (1,2-dimyristoleoyl-sn-glycero-3-ethylphosphocholine (Tf salt)). In some embodiments, the lipid is dimethyl dioctadecyl ammonium bromide (DDAB) or 1,2-dioleoyl-3-trimethylammonium-propane (DOTAP). In some embodiments, the QNS-lipid composite carrier encapsulates an active agent (e.g., a drug such as a chemotherapy agent). In some embodiments, a QNS-lipid composite carrier has a diameter of 100-1000 nm (e.g., 100, 150, 200, 250, 300, 350, 400, 450, 500, 550, 600, 650, 700, 750, 800, 850, 900, 950, 1000, or ranges therebetween). In some embodiments, the QNS-lipid composite carrier comprises QNSs of at least two different sizes. In some embodiments, QNSs comprise a semiconducting core material comprising, for example, ZnS, or another suitable semiconducting material. In some embodiments, QNSs comprise a hydrophilic surface layer. In some embodiments, the QNS is a surface-functionalized quantum dot.

In some embodiments, provided herein are NP-lipid composite carriers comprising a shell of upconverting nanostructures (UNS). In some embodiments, provided herein are UNS-lipid composite carriers (ULCC). In some embodiments, the UNS is an upconverting nanoparticle (e.g., $Y_2O_3$, $ZrO_2$, $NaYF_4$, $YVO_4$, $Y_2O_2S$, GdOCl, or combinations thereof) with a functionalized surface. In some embodiments, a UNS-lipid composite carrier comprises core NPs that are surface functionalized with a hydrophilic surface layer (e.g., a negatively-charged moiety, citrate, etc.). In some embodiments, the hydrophilic surface layer comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the hydrophilic surface layer comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the UNS is 2-20 nm (e.g., 2, 4, 6, 8, 10, 12, 14, 16, 18, 20, or ranges therebetween). In some embodiments, provided herein UNS-lipid composite carriers (PLCCs), comprising: a hydrophobic core comprising a plurality of lipid tails and a shell comprising UNSs assembled on a plurality of lipid heads. In some embodiments, the UNSs are functionalized with a negatively charged moiety (e.g., citrate). In some embodiments, the negatively charged moiety comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the lipid is a cationic lipid. In some embodiments, the lipid is an amphiphilic surfactants (e.g., comprising one or more hydrocarbon or fluorocarbon tails) and amphiphilic polymers with cationic head group (e.g., Cetrimonium bromide (CTAB), Cetylpyridinium chloride (CPC), Benzalkonium chloride (BAC), Benzethonium chloride (BZT), Dimethyldioctadecylammonium chloride, Dioctadecyldimethylammonium bromide (DODAB), etc.). In some embodiments, the lipid is a cationic lipid selected from DOTMA (1,2-di-O-octadecenyl-3-trimethylammonium propane (chloride salt)), DOBAQ (N-(4-carboxybenzyl)-N,N-dimethyl-2,3-bis(oleoyloxy)propan-1-aminium), 14:0 DAP (1,2-dimyristoyl-3-dimethylammonium-propane), 16:0 DAP (1,2-dipalmitoyl-3-dimethylammonium-propane), 18:0 DAP (1,2-distearoyl-3-dimethylammonium-propane), DODAP (1,2-dioleoyl-3-dimethylammoniumpropane), DORIE (1,2-dioleyloxypropyl-3-dimethyl-hydroxyethylammonium bromide), DMRIE (1,2-dimyristyloxypropyl-3-dimethyl-hydroxyethylammonium bromide), GAP-DLRIE ((±+)-N-(3-aminopropyl)-N,N-dimethyl-2,3-bis(dodecyloxy)-1-propanaminium bromide), diC14-amidine (N-t-butyl-N'-tetradecyl-3-tetradecylamino-propionamidine), DOGS (Di-octadecyl-amido-glycyl-spermine), DOSPA ((+)-N,N-dimethyl-N-[2-(sperminecar-box-amido)ethyl]-2,3-bis(dioleyloxy)-1-propaniminium pentahy-drochloride), DC-Cholesterol.HCl (3β-[N-(N',N'-dimethylaminoethane)-carbamoyl]cholesterol hydrochloride), GL67 (N4-Cholesteryl-Spermine HCL salt), BGTC (bis (guanidinium)-tren-cholesterol), MVL5 (N1-[2((1S)-1-[(3-aminopropyl)amino]-4-[di(3-amino-propyl)amino]butylcarboxamido)ethyl]-3,4-di[oleyloxy]-benzamide), 12:0 EPC (Cl Salt) (1,2-dilauroyl-sn-glycero-3-ethylphosphocholine (chloride salt)), 14:0 EPC (Cl Salt) (1,2-dimyristoyl-sn-glycero-3-ethylphosphocholine (chloride salt)), 16:0 EPC (Cl Salt) (1,2-dipalmitoyl-sn-glycero-3-ethylphosphocholine (chloride salt)), 18:0 EPC (Cl Salt) (1,2-distearoyl-sn-glycero-3-ethylphosphocholine (chloride salt)), 18:1 EPC (Cl Salt) (1,2-dioleoyl-sn-glycero-3-ethylphosphocholine (chloride salt)), 16:0-18:1 EPC (Cl Salt) (1-palmitoyl-2-oleoyl-sn-glycero-3-ethylphosphocholine (chloride salt)), and 14:1 EPC (Tf Salt) (1,2-dimyristoleoyl-sn-glycero-3-ethylphosphocholine (Tf salt)). In some embodiments, the lipid is dimethyl dioctadecyl ammonium bromide (DDAB) or 1,2-dioleoyl-3-trimethylammonium-propane (DOTAP). In some embodiments, the PNS-lipid composite carrier encapsulates an active agent (e.g., a drug such as a chemotherapy agent). In some embodiments, a UNS-lipid composite carrier has a diameter of 100-1000 nm (e.g., 100, 150, 200, 250, 300, 350, 400, 450, 500, 550, 600, 650, 700, 750, 800, 850, 900, 950, 1000, or ranges therebetween). In some embodiments, the UNS-lipid composite carrier comprises UNSs of at least two different sizes.

In some embodiments, provided herein are NP-lipid composite carriers comprising a nanostructures shell comprising nanoparticles of $SiO_2$, $CeO_2$, $TiO_2$, C, and/or $MoS_2$.

Further embodiments provide a system, comprising a) the NP-lipid composite carriers described herein (e.g., MLCCs, QLCCs, PLCCs, UNCCs, etc.); and b) a device for generating a radio frequency, wherein the NP-lipid composite carriers generate heat and/or release an encapsulated cargo (e.g., drug) when exposed to a radio frequency generated by the radio frequency generator.

In some embodiments, embodiments herein described for use with MNS-lipid composite carriers also find use with QNS-lipid composite carriers and/or PNS-lipid composite carriers. In some embodiments, appropriate adjustments to such embodiments will be apparent from the description herein. Embodiments comprising MLCCs, QLCCs, and/or PLCCs are within the scope herein.

Additional embodiments provide an MRI contrast agent comprising the NP-lipid composite carriers (e.g., MLCCs, QLCCs, PLCCs, ULCCs, etc.) described herein.

Other embodiments provide a pharmaceutical composition comprising the NP-lipid composite carriers (e.g., MLCCs, QLCCs, PLCCs, ULCCs, etc.) described herein and a pharmaceutically acceptable carrier.

In some embodiments, provided herein are methods, comprising a) administering the NP-lipid composite carriers (e.g., MNS-lipid composite carriers) described herein to a cell; and c) destroying the cell by exposing the NP-lipid composite carriers (e.g., MNS-lipid composite carriers) to a radio frequency that causes the NP-lipid composite carriers (e.g., MNS-lipid composite carriers) to generate heat. In some embodiments, the NP-lipid composite carriers (e.g., MNS-lipid composite carriers) releases its cargo (e.g., a drug) when the magnetic-lipid composite nanoparticle is exposed to the radio frequency. In some embodiments, the cell is a cancer cell. In some embodiments, the cell is in a subject.

Some embodiments provide methods, comprising a) administering the NP-lipid composite carriers (e.g., MNS-lipid composite carriers) described herein, wherein the NP-lipid composite carriers (e.g., MNS-lipid composite carriers) comprise a drug (e.g., encapsulate a drug cargo); and b) releasing the drug.

In some embodiments, the methods further comprise the step of imaging the NP-lipid composite carriers (e.g., MNS-lipid composite carriers) using MRI.

Certain embodiments provide methods, comprising: a) contacting a cell with the NP-lipid composite carriers (e.g., MNS-lipid composite carriers) described herein; and b) imaging the NP-lipid composite carriers (e.g., MNS-lipid composite carriers) using MRI.

Embodiments herein provide methods of synthesizing the NP-lipid composite carriers (e.g., MLCCs, QLCCs, PLCCs, ULCCs, etc.), comprising: contacting lipids with nanostructures (e.g., MLCCs, QLCCs, PLCCs, ULCCs, etc.) under conditions such that the NP-lipid composite carriers (e.g., MLCCs, QLCCs, PLCCs, ULCCs, etc.) comprising a hydrophobic core comprising a plurality of lipid tails and a shell comprising nanostructures assembled on a plurality of lipid heads is self-assembled.

Additional embodiments are described herein.

The T2 relaxation time from the cell pellets at different concentration of magnetic-lipid composite nanoparticles.

Figure 10:
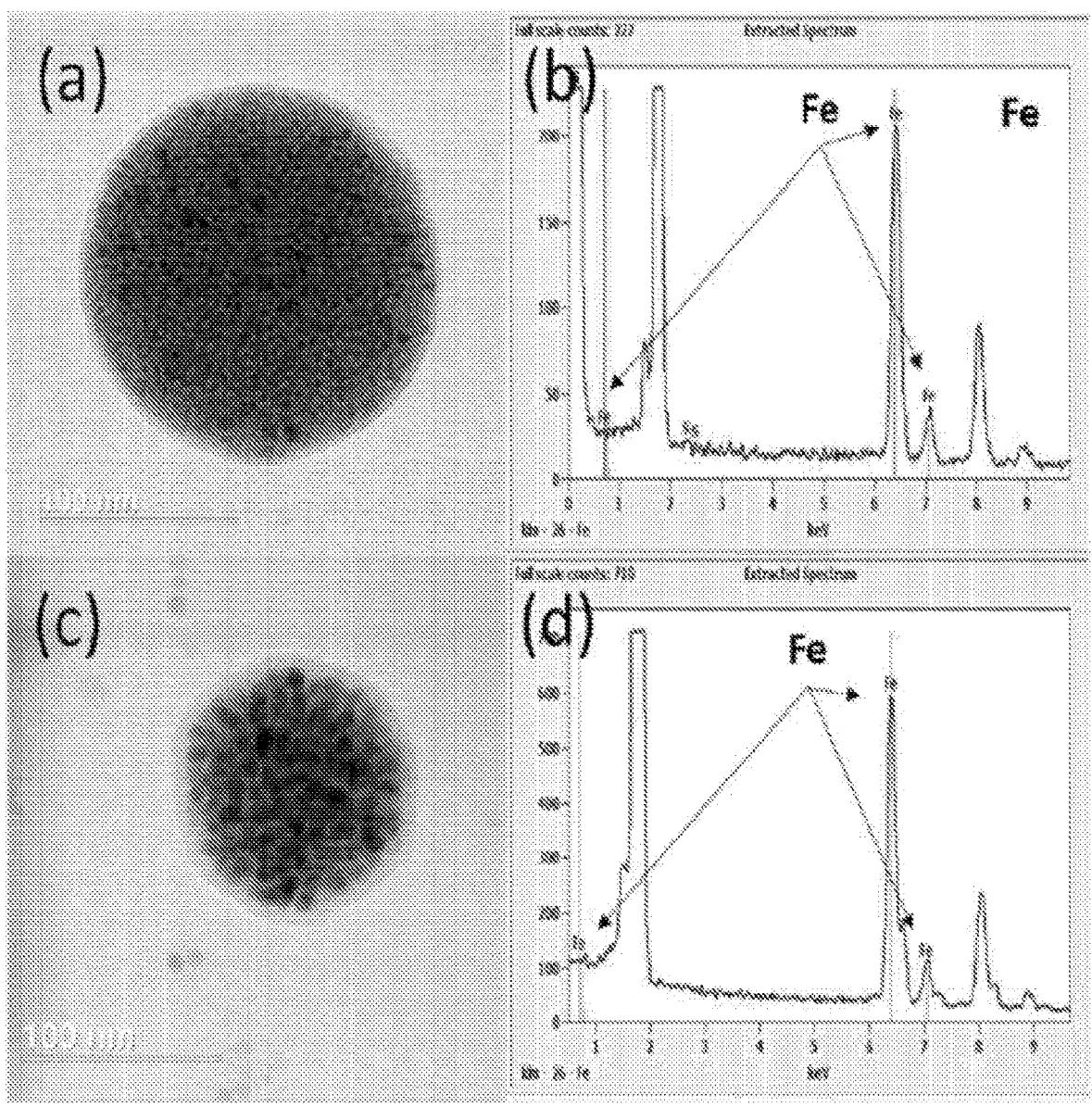
Figure 10:
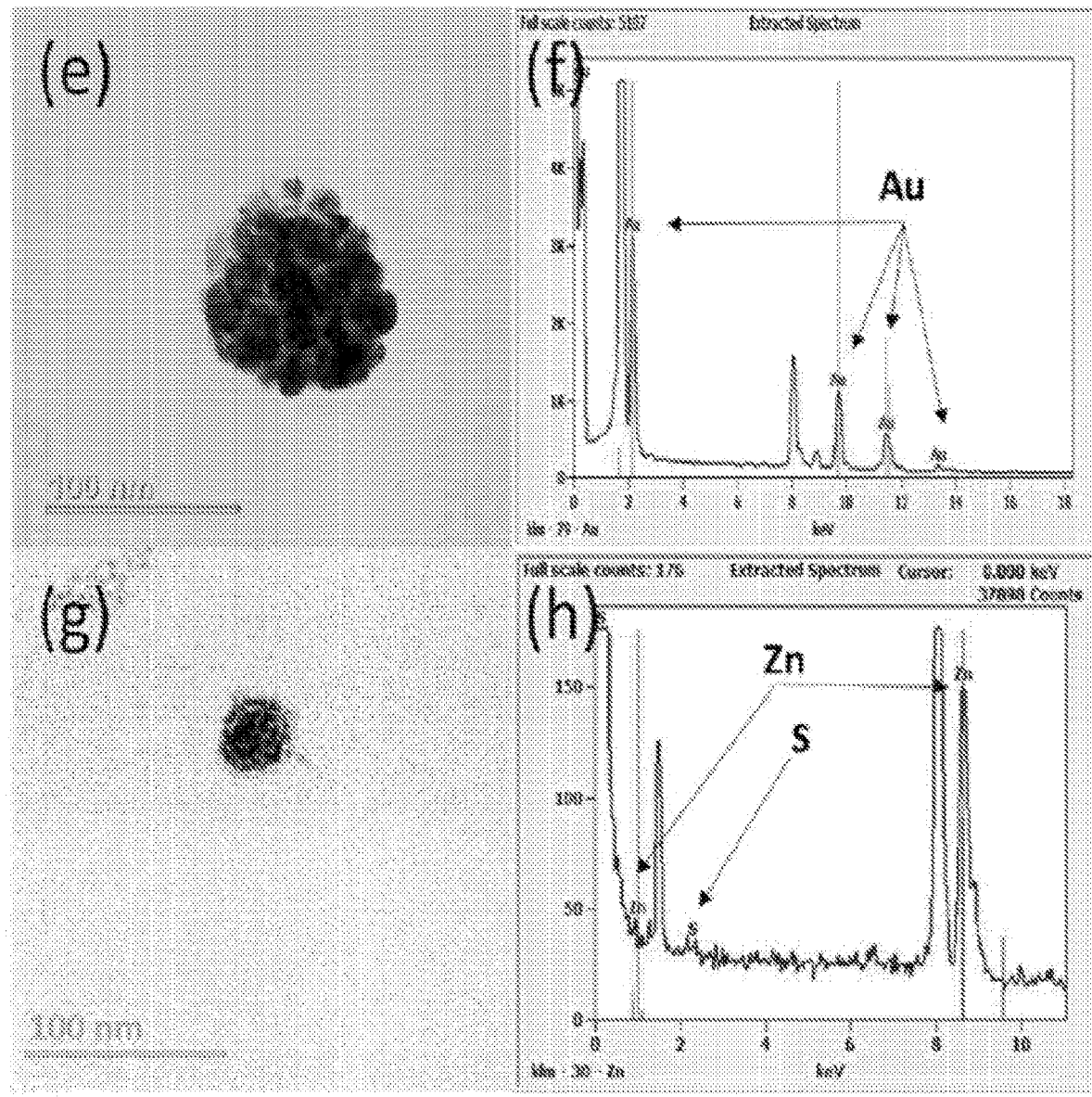

FIG. 10. TEM and EDX of (a,b) 180 nm magnetic-lipid composite carriers from 4 nm $Fe_3O_4$ nanoparticles, (c,d) 100 nm magnetic-lipid composite carriers from 8 nm $Fe_3O4$ nanoparticles, (e,f) 100 nm plasmonic-lipid composite carriers from 13 nm Au NPs, and (g,h) 40 nm semiconducting-lipid composite nanoparticles from 6 nm ZnS quantums dots.

Figure 11:
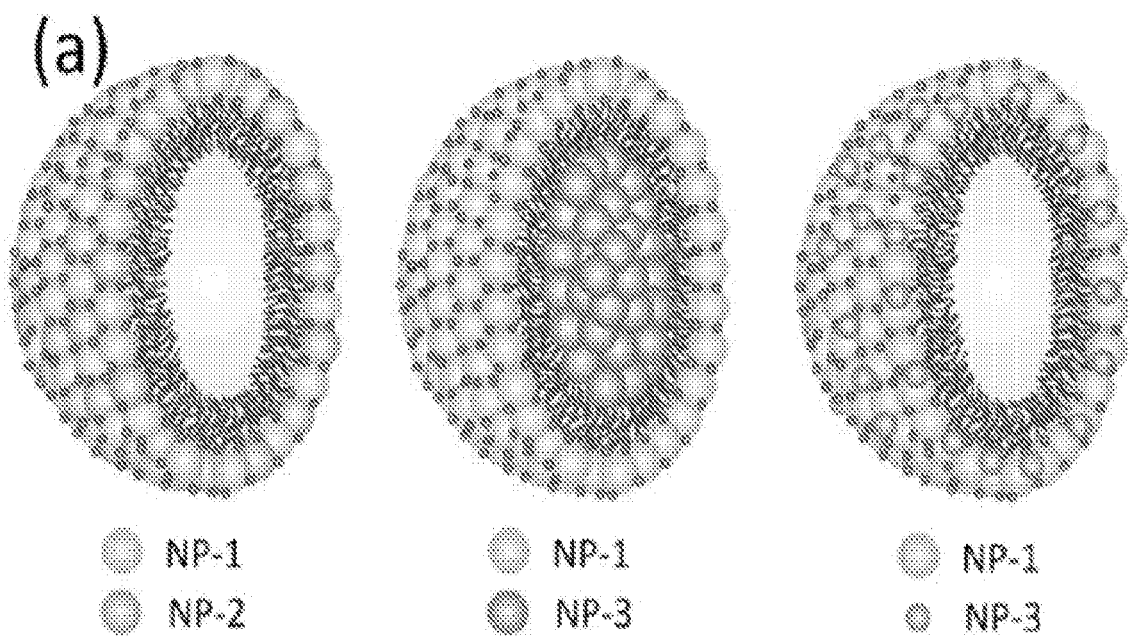
Figure 11:
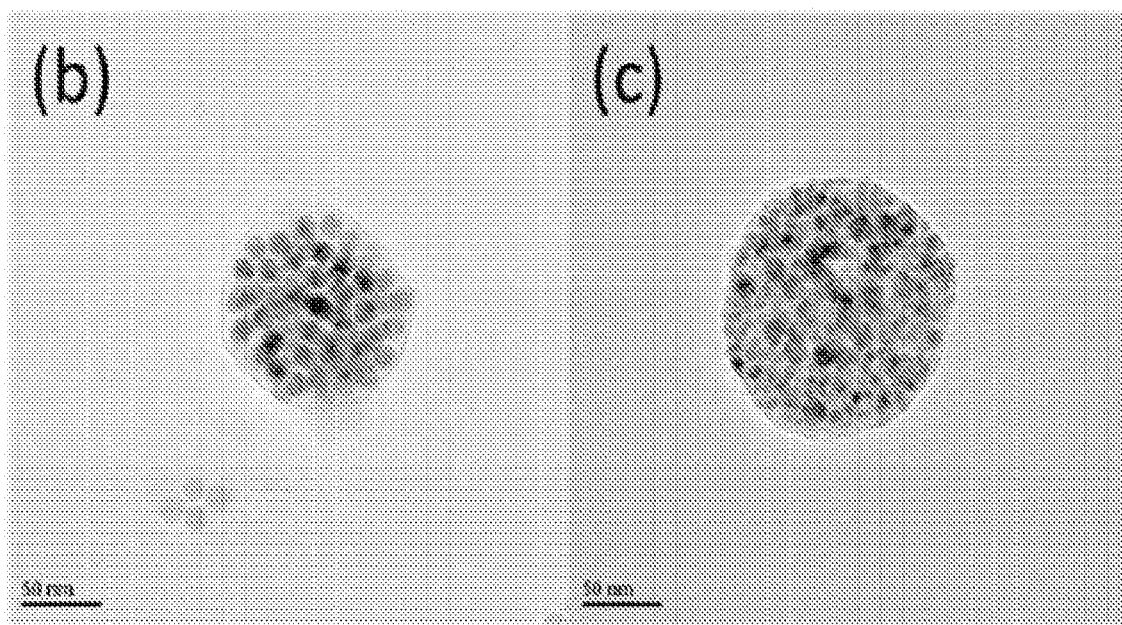

FIG. 11. (a) Schematic to fabricate multifunctional hybrid structures using combination of nanoparticles of different types/size. (b) magnetic-lipid composite nanoparticles with 18 nm MNS (c) magnetic-lipid composite carriers with 18 and 8 nm MNS.

Figure 12:
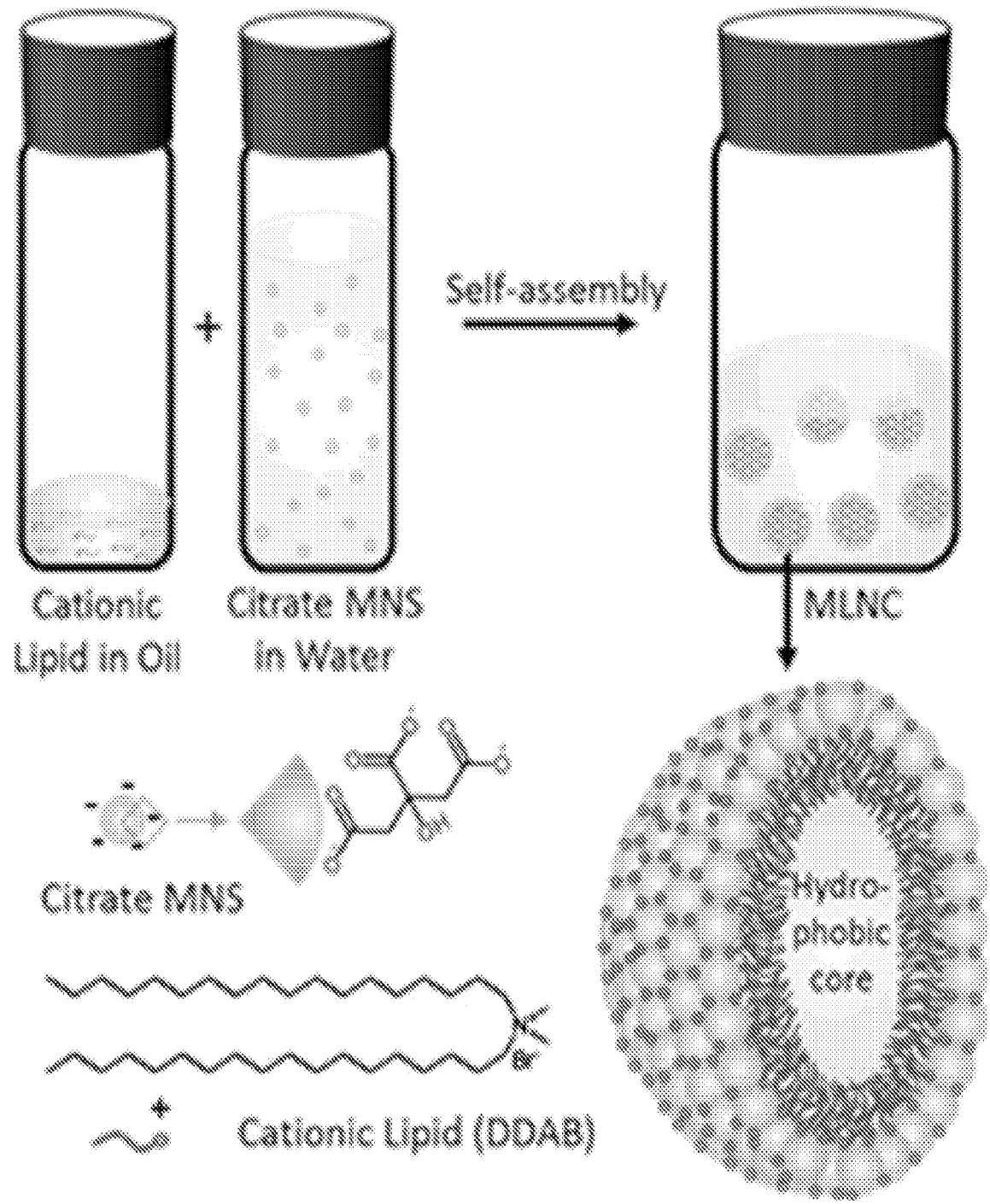

FIG. 12. Schematic of NP-lipid composite carrier self-assembly.

Figure 13:
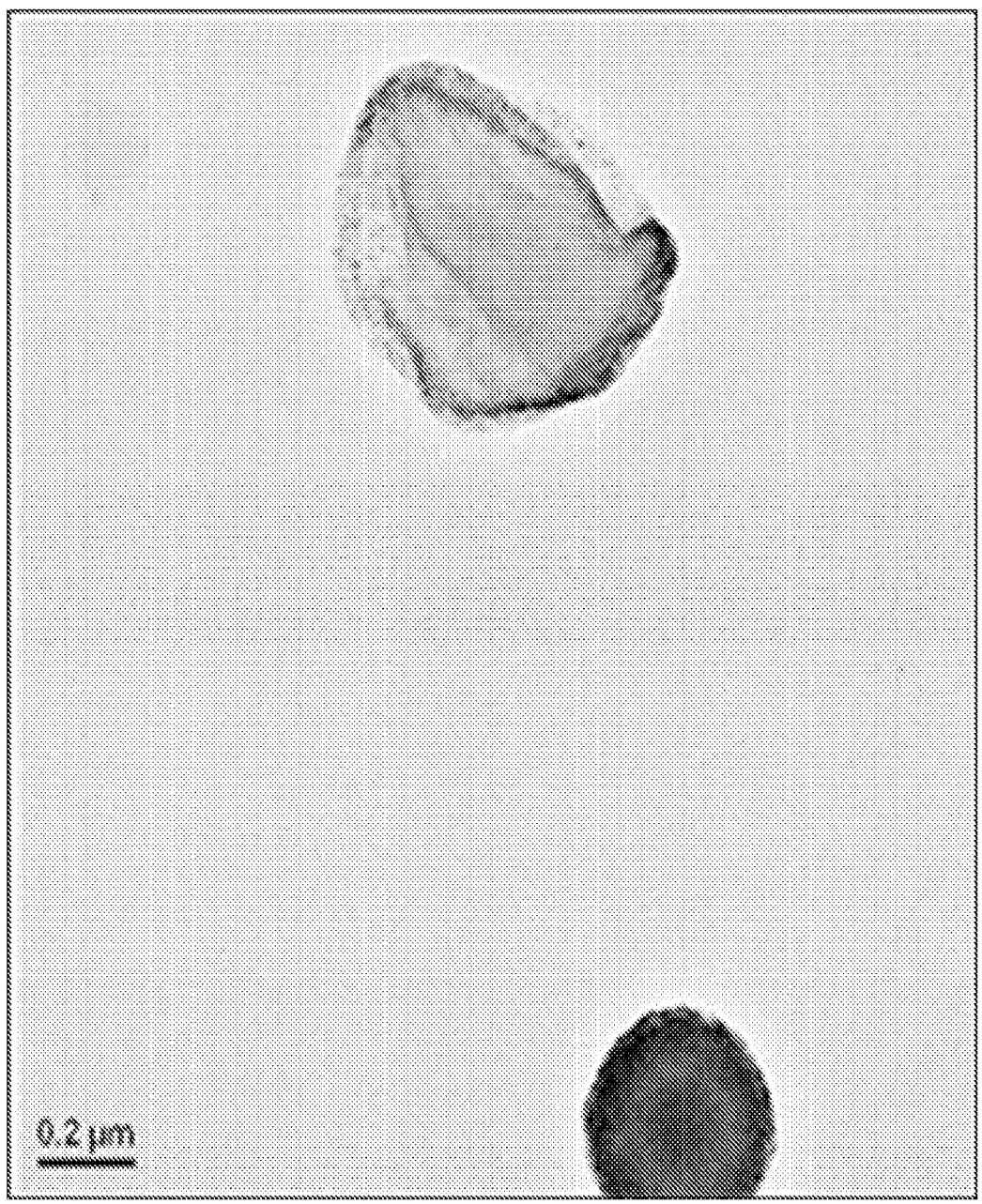

FIG. 13. TEM of a collapsed magnetic-lipid composite carriers.

Figure 14:
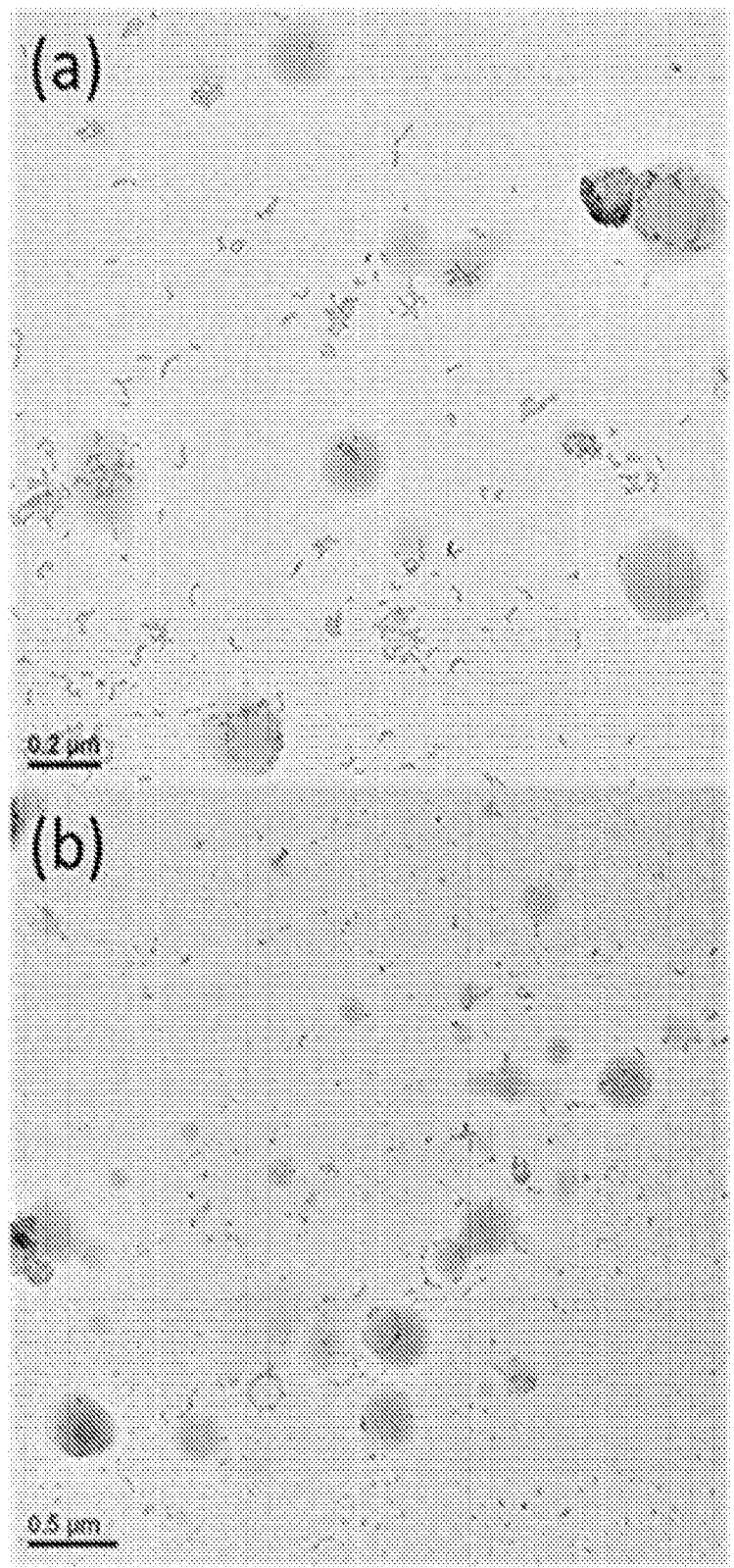

FIG. 14. TEM of control experiments (a) Mixture of cationic MNS with cationic lipid (b) citrate MNS with neutral lipid (DPPC).

Figure 15:
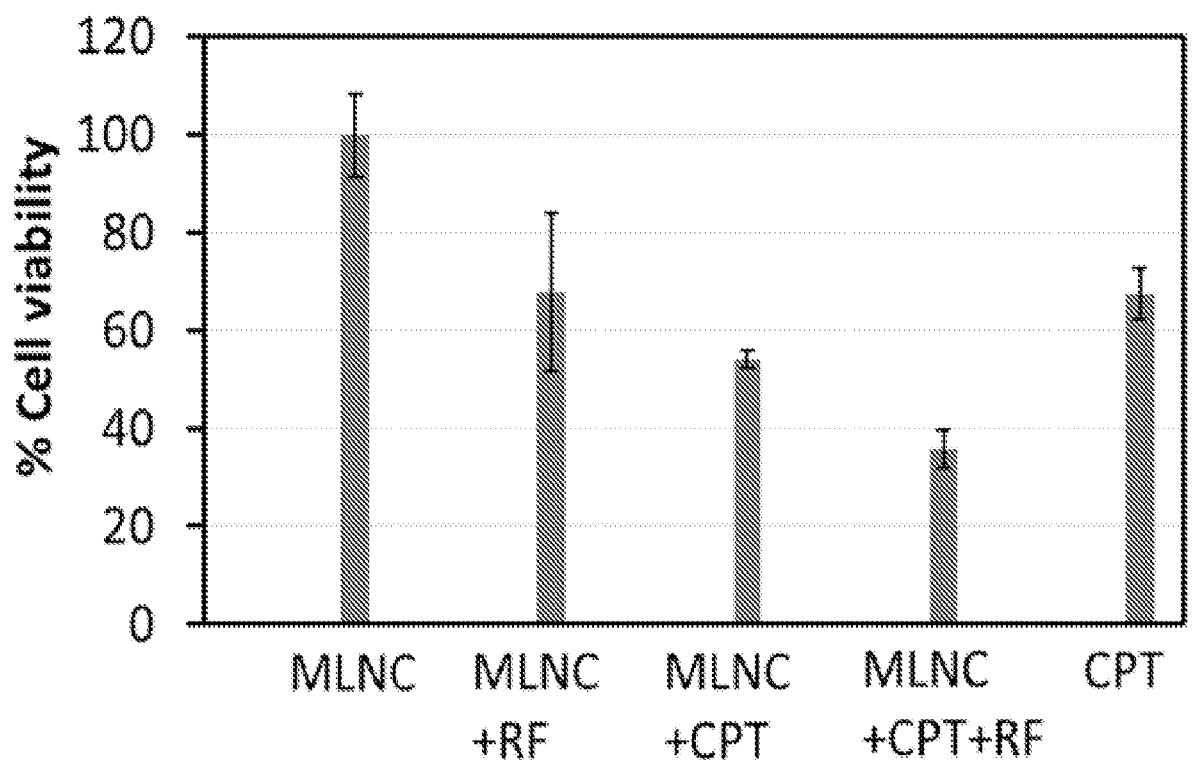

FIG. 15. Cytotoxicity study of HepG2 cancer cells when treated by combination therapy or single treatments with different concentrations of MLCCs with/without Cisplatin (CPT) and with/without the application of RF field. Cell viability was assessed 24 h after treatment.

DEFINITIONS

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "theranostic agent" is a reference to one or more theranostic agents and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C." As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "agent" refers to a composition that possesses a biologically relevant activity or property. Biologically relevant activities are activities associated with biological reactions or events or that allows the detection, monitoring, or characterization of biological reactions or events. Biologically relevant activities include, but are not limited to, therapeutic activities (e.g., the ability to improve biological health or prevent the continued degeneration associated with an undesired biological condition), targeting activities (e.g., the ability to bind or associate with a biological molecule or complex), monitoring activities (e.g., the ability to monitor the progress of a biological event or to monitor changes in a biological composition), imaging activities (e.g., the ability to observe or otherwise detect biological compositions or reactions), and signature identifying activities (e.g., the ability to recognize certain cellular compositions or conditions and produce a detectable response indicative of the presence of the composition or condition). The agents of the present invention are not limited to these particular illustrative examples. Indeed any useful agent may be used including agents that deliver or destroy biological materials, cosmetic agents, and the like.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "nanoparticle" refers to a particle having dimensions between 1 and 1000 nanometers. A nanoparticle may or may not exhibit one or more size-related properties that differ significantly from those observed in larger particles or bulk materials.

As used herein, the term "biocompatible" refers to materials, compounds, or compositions means that do not cause or elicit significant adverse effects when administered to a subject. Examples of possible adverse effects that limit biocompatibility include, but are not limited to, excessive inflammation, excessive or adverse immune response, and toxicity.

DETAILED DESCRIPTION OF THE INVENTION

Provided herein are nanoparticle-lipid composite carriers as theranostic agents, particularly for diagnosis and/or treatment of cancers and related diseases and conditions. In particular embodiments, the carrier composites comprise a lipid core and an outer shell of functionalized nanoparticles (fNPs).

Provided herein is a versatile synthesis of nanoparticle-lipid composite carriers (e.g., MNS-lipid composite carriers, PNS-lipid composite carriers, QNS-lipid composite carriers, etc.) that finds use in research, screening, diagnostic and therapeutic applications. Self-assembly of magnetic nanostructures (MNS) or other nanostructures (e.g., PNS, QNS, etc.) and lipids with complementary functional groups results in NP-lipid composite carriers with NSs and lipid head sassembling on the surface and a hydrophobic core produced from lipid tails. The hydrophobic core provides a compartment for loading of therapeutic cargo loading (e.g., 80% encapsulation efficiency). For MNS-lipid composite carriers, cargo release is actuated via RF field induced thermal activation of MNS. From a diagnostic perspective, MNS-lipid composite carriers show 8.5 times higher contrast ($r_2$ relaxivity up to 680 mM$^{-1}$s$^{-1}$) in magnetic resonance imaging (MRI) than commercially available $T_2$ MRI contrast agent (Ferumoxytol®). The high MR contrast allowed MRI of liver hepatocellular carcinoma (HepG2) cells that have internalized MNS-lipid composite carriers. Paclitaxel (PTX) loaded MNS-lipid composite carriers internalised into HepG2 cells caused 75% cell death with RF field exposures. Imaging with high signal/noise ratio and treatment with high efficacy demonstrates the magnetic-lipid composite nanoparticles as theranostic agents. Experiments conducted during development of embodiments herein demonstrate that this method can be extended to synthesize MNS-lipid composite carriers with MNSs of different sizes (e.g., 4 to 20 nm).

Similarly, experiments conducted during development of embodiments herein demonstrate NP-lipid composite carriers comprising NPs of different types (e.g., MNS, PNS (Au), QNS (quantum dots), etc.), making it a versatile approach to produce multifunctional nanohybrids. NP-lipid composite carriers comprising plasmonic and/or semiconducting NPs exhibit functionalities consistent with the type of NP incorporated.

I. NP-Lipid Composite Carriers

In some embodiments, provided herein is a nanoparticle stabilized lipid composite carrier, comprising: a hydrophobic core comprising a plurality of lipid tails and a shell comprising nanostructures (e.g., surface-functionalize NPs) assembled on a plurality of lipid heads. In some embodiments, the nanostructure is functionalized with a negatively charged moiety (e.g., citrate).). In some embodiments, the negatively charged moiety comprises a salt or ester of an acid, such as acetate, oxalate, citrate, phthalate, lactate, propionate, butyrate, phosphate, phosphite, sulfate, sulfite, sulfonate, carboxylate, nitrate, nitrite, arsenate, silicate, carbonate, hypochlorite, chlorite, chlorate, perchlorate, permanganate, dichromate, chromate, bromate, and higher fatty acid salts. In some embodiments, the lipid is a cationic lipid. In some embodiments, the lipid is an amphiphilic surfactants (e.g., comprising one or more hydrocarbon or fluorocarbon tails) and amphiphilic polymers with cationic head group (e.g., Cetrimonium bromide (CTAB), Cetylpyridinium chloride (CPC), Benzalkonium chloride (BAC), Benzethonium chloride (BZT), Dimethyldioctadecylammonium chloride, Dioctadecyldimethylammonium bromide (DODAB), etc.). In some embodiments, the lipid is a cationic lipid selected from DOTMA (1,2-di-O-octadecenyl-3-trimethylammonium propane (chloride salt)), DOBAQ (N-(4-carboxybenzyl)-N,N-dimethyl-2,3-bis(oleoyloxy)propan-1-aminium), 14:0 DAP (1,2-dimyristoyl-3-dimethylammonium-propane), 16:0 DAP (1,2-dipalmitoyl-3-dimethylammonium-propane), 18:0 DAP (1,2-distearoyl-3-dimethylammonium-propane), DODAP (1,2-dioleoyl-3-dimethylammonium-propane), DORIE (1,2-dioleyloxypropyl-3-dimethylhydroxyethylammonium bromide), DMRIE (1,2-dimyristyloxypropyl-3-dimethyl-hydroxyethylammonium bromide), GAP-DLRIE ((±+)-N-(3-aminopropyl)-N,N-dimethyl-2,3-bis(dodecyloxy)-1-propanaminium bromide), diC14-amidine (N-t-butyl-N'-tetradecyl-3-tetradecylaminopropionamidine), DOGS (Di-octadecyl-amido-glycyl-spermine), DOSPA ((+)-N,N-dimethyl-N-[2-(sperminecar-boxamido)ethyl]-2,3-bis(dioleyloxy)-1-propaniminium pentahy-drochloride), DC-Cholesterol·HCl (3β[N-(N'N,N'-dimethylaminoethane)-carbamoyl]cholesterol hydrochloride), GL67 (N4-Cholesteryl-Spermine HCL salt), BGTC (bis (guanidinium)-tren-cholesterol), MVL5 (N1-[2-((1S)-1-[(3-aminopropyl)amino]-4-[di(3-amino-propyl)amino]butylcarboxamido)ethyl1]-3,4-di[oleyloxy]-benzamide), 12:0 EPC (Cl Salt) (1,2-dilauroyl-sn-glycero-3-ethylphosphocholine (chloride salt)), 14:0 EPC (Cl Salt) (1,2-dimyristoyl-sn-glycero-3-ethylphosphocholine (chloride salt)), 16:0 EPC (Cl Salt) (1,2-dipalmitoyl-sn-glycero-3-ethylphosphocholine (chloride salt)), 18:0 EPC (Cl Salt) (1,2-distearoyl-sn-glycero-3-ethylphosphocholine (chloride salt)), 18:1 EPC (Cl Salt) (1,2-dioleoyl-sn-glycero-3-ethylphosphocholine (chloride salt)), 16:0-18:1 EPC (Cl Salt) (1-palmitoyl-2-oleoyl-sn-glycero-3-ethylphosphocholine (chloride salt)), and 14:1 EPC (Tf Salt) (1,2-dimyristoleoyl-sn-glycero-3-ethylphosphocholine (Tf salt)). In some embodiments, the lipid is dimethyl dioctadecyl ammonium bromide (DDAB) or 1,2-dioleoyl-3-trimethylammonium-propane (DOTAP). In some embodiments, the composite carrier encapsulates an active agent (e.g., a drug such as a chemotherapy agent). In some embodiments, the nanostructure is a magnetic nanoparticle, plasmonic nanoparticle, or semiconducting nanoparticle. In some embodiments, the nanoparticle has a diameter of 2-20 nm (e.g., 2, 4, 6, 8, 10, 12, 14, 16, 18, 20 nm, or other size). In some embodiments, the composite carrier comprises nanoparticles of at least two different sizes. In some embodiments, the nanoparticles comprise a material selected from, for example, $MFe_2O_4$ (wherein M is Fe, Mn, $Zn_{0.2}Mn0.8$, etc.), Au, or ZnS. In some embodiments, composite carriers are self-assembled as described, for example, in Example 1 below.

In some embodiments, MNS comprise a nanomaterial which includes a magnetic nanocomponent coated by a single or multiple layer(s) of non-toxic metal oxide(s), with or without inclusion of quantum dot materials; optionally comprising a bio-inert surface coating with or without addition of bioactive polymers or bio-molecules, depending on the different application purposes. In some embodiments, a PNS or QNS is a nanostructure with similar properties to the MNS described above, but with distinct core properties.

In some embodiments, nanostructures are composed of aggregation or assembly at a coarser scale of smaller nanoparticles.

In some embodiments, MNS comprise a magnetic core of $MnFe_2O_4$ or $NiFe_2O_4$. In some embodiments, the magnetic material is spherical, while in other embodiments it is irregular in shape (e.g., rods, needles or prisms). In some embodiments, the magnetic core is coated with a non-magnetic shell for use in attaching targeting agents. In some embodiments, a PNS or QNS is a nanostructure with similar properties to the MNS described above, but with distinct core properties (e.g., Au or ZnS core).

In some embodiments, the magnetic nanocomponent in the nanomaterial is a precursor for $\alpha$-$Fe_2O_3$, $\gamma$-$Fe_2O_3$ or related nanoalloy oxides with Fe after oxidization or for bcc-Fe or alloys-based Fe nanocomponents after reducing. The magnetic nanocomponent in the nanomaterials based on iron oxide can be extended to other iron oxide based nanomaterials, including, but not limited to, $MFe_2O_4$, $RFeO_3$, and $MRFeO_x$ (M=Ba, Bi, Co, Cr, Cu, Fe, Mg, Mn, Ni, Ti, Y, Zn) (R=rare earth metal elements) nanomaterials, and iron oxide coated various nanomaterials. In some embodiments, nanomaterials are $FeO_2$ nanoparticles.

The size of the completed nanomaterials in at least one dimension is preferably within 0.1-1000 nm. The shape of the nanomaterials may be regular (column, cube, cylinder, pillar, pyramid, rod, sphere, tube etc.) or irregular/random. The shape of the nanomaterials is controlled by adjusting the reaction dynamics and aging/ripening time.

In some embodiments, the NP-lipid composite carriers are nanocapsules.

In some embodiments, a therapeutic agent (e.g., drug) is encapsulated within the composite carriers herein. The present invention is not limited to a particular drug. In some embodiments, the drug is a known chemotherapeutic agent (see below). In some embodiments, the chemotherapeutic agent is an agent known to be useful in treating cancer.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In some embodiments, anticancer agents comprise agents that induce or stimulate apoptosis. Agents that induce apoptosis include, but are not limited to, radiation (e.g., X-rays, gamma rays, UV); tumor-derived growth factor ligands, receptors, and analogs; kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORA-DEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycoformycin)).

In still further embodiments, chemotherapeutic agents suitable for use in the compositions and methods of the present invention include, but are not limited to: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2, 4, 6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[pentyloxy)carbonyl]-cytidine) | Xeloda | Roche |
| Carboplatin (platinum, diammine [1,1-cyclobutanedicarboxylato(2-)-0, 0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |

TABLE 1-continued

| | | |
|---|---|---|
| Darbepoetin alfa (recombinant peptide) | Aranesp | Amgen, Inc., Thousand Oaks, CA |
| daunorubicin liposomal ((8 S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2 R,3 S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8 S,10 S)-10-[(3-amino-2,3,6-trideoxy-a-L-lyxo-hexopyranosyl)oxy-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8 S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3, 17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |

TABLE 1-continued

| | | |
|---|---|---|
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)[6],Azgly[10]]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator titmetan [N-[2-bis(carboxymethyl)amino]-3-(p-isothiocyanatophenyl)-propyl]-[N-[2-bis(carboxymethyl)amino]-2-(methyl) ethyl]glycine) | Zevalin | Biogen IDEC, Inc., Cambridge MA |
| Idarubicin (5, 12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7 S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4 S)-4,11-diethyl-4-hydroxy-9-[(4-piperi-dinopiperidino)carbonyloxy]-1H-pyrano[3',4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-l-ylmethylene) dibenzonitrile) | Femara | Novartis |
| Leucovorin (L-Glutamic acid, N[4[[(2amino-5-formyl-1,4,5,6,7,8 hexahydro4oxo6-pteridinl)methyl]amino]benzoyl], calcium salt (1:1)) | Wellcovorin, Leucovorin | Immunex, Corp., Seattle, WA |
| Levamisole HCl ((-)-(S)-2,3,5, 6-tetrahydro-6-phenylimidazo [2,1-b] thiazole monohydrochloride $C_{11}H_{12}N_2S$•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |

TABLE 1-continued

| | | |
|---|---|---|
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexane-diamine-N,N'] [oxalato(2-)-O,O'] platinum) | Eloxatin | Sanofi Synthelabo, Inc., NY, NY |
| Paclitaxel (5β, 20-Epoxy-1,2a, 4,7β, 10β, 13a-hexahydroxytax-11-en-9-one 4,10-diacetate 2-benzoate 13-ester with (2R, 3 S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |

TABLE 1-continued

| Drug | Brand | Company |
|---|---|---|
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3', 4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown,NJ |
| Tositumomab, I 131 Tositumomab (recombinant murine immunotherapeutic monoclonal $IgG_{2a}$ lambda anti-CD20 antibody (1131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech,Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2 S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUCl-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpimase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Eds. Hardman et al., 2001.

In some embodiments, the drug is an siRNA drug. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

II. Therapeutic Applications

As described above, embodiments of the present invention provide methods, systems and compositions for treating disorders (e.g. cancers). In some embodiments, drugs for treating a particular condition (e.g., cancer) are encapsulated within the composite carriers described herein. Following delivery of the composite carriers comprising a drug to the site of disease (e.g., using local delivery or my incorporating a targeting agent into the composite carrier), the drug is released. In some embodiments, radio frequency administration is used to release the drug and/or provide further killing of diseased tissue (e.g., cancer cells).

For example, in some embodiments, composite carriers are heat activated in order to destroy cancerous tissue. In some embodiments, the size of NPs (e.g., MNSs) included in the composite nanoparticle is optimized for treatment (e.g., heat therapy). For example, in some embodiments, smaller particles are optimal for heat inactivation. In some embodiments, a radio frequency (RF) field generated by an RF generator or a magnetic field generated by a magnetic field generator is utilized to provide heat for heat therapy of cancerous tissue.

In some embodiments, dosing schedules are calculated from measurements of drug accumulation in the body of the patient. The administering clinician determines optimum dosages, dosing methodologies, and repetition rates. Optimum dosages may vary depending on the relative potency of individual therapeutics, and can generally be estimated based on EC50s found to be effective in in vitro and in vivo animal models or based on the examples described herein. For example, in some embodiments dosage is from 0.01 µg to 100 g per kg of body weight, and may be given once or more daily, weekly, monthly or yearly. The treating clinician estimates repetition rates for dosing based on measured residence times and concentrations of the drug in bodily fluids or tissues. In some embodiments, following successful treatment, the subject undergoes maintenance therapy to prevent the recurrence of the disease state.

III. Diagnostic Applications

In some embodiments, provided herein are compositions and methods for diagnostic applications. For example, in some embodiments, diagnostic applications are used to image and define tumor boundaries. Such images find use, for example, prior to and during surgical removal of tumors and for therapeutic targeting of tumors.

In some embodiments, composite carriers comprise or serve as a contrast agent for imaging (e.g., X-Ray, computed tomography (CT) imaging, or MRI imaging).

In some embodiments, nanoparticles are used in research (e.g., imaging in animal models, structural studies, DNA-protein binding interactions, protein capture, etc.) or drug screening applications.

IV. Kits and Systems

In some embodiments, the present invention provides kits for using in research, diagnostic and therapeutic applications. In some embodiments, kits include components necessary, sufficient or useful in performing the methods of embodiments of the present invention.

In some embodiments, kits include composite carriers herein, drugs for use in combination therapy, along with any controls, buffers, reagents, administration tools, etc.

Kits may further comprise appropriate controls and/or detection reagents. Any one or more reagents that find use in any of the methods described herein may be provided in the kit.

In some embodiments, the present invention provides systems for use in targeting and treating disease (e.g., cancer). In some embodiments, systems comprise the above described components and a device for generating a radio frequency (RF) for use in drug release and/or therapy.

EXPERIMENTAL

The following examples are provided in order to demonstrate and further illustrate certain preferred embodiments and aspects of the present invention and are not to be construed as limiting the scope thereof.

Example 1

Experimental
Synthesis of Citrate or Amine MNS $MFe_2O_4$ (M=Fe, Mn, $Zn_{0.2}Mn_{0.8}$) nanoparticles were used as magnetic core of MNS and were synthesized using previously reported thermal decomposition method (Refs. 4b, 13; herein incorporated by reference in their entireties). The as-synthesized oleic acid coated hydrophobic $MFe_2O_4$ nanoparticles were functionalized with citrate or dopamine, via ligand exchange process, resulting in negative or positive charged MNS. (scheme 1; FIG. 12) (Ref 4b; herein incorporated by reference in its entirety). The particle diameters and size distribution of NP-lipid composite carriers were determined from TEM and DLS. The final concentration of the Fe in MNS was determined by ICP-MS analysis. The NP-lipid composite carriers demonstrated high colloidal stability across a wide pH range (pH 6-10) and cell culture medium.

Synthesis of MNS-Lipid Composite Carriers

MNS-lipid composite carriers (MLCC) were synthesized by mixing citrate MNS and cationic lipid dimethyl dioctadecyl ammonium bromide (DDAB). For synthesis of 100 nm MLCCs, 10 µL aqueous dispersion of citrate MNS (1-4 mg/ml of Fe), 10 µL chlorofrom dispersion of DDAB (5-25 mg/ml), and 480 µL of Milli-q water was emulisified for 30 seconds and left overnight at room temperature for self-assembly. The mixture was centrifuged to remove MNS that didn't participate in assembly formation and dialyzed to remove any residual surfactants and lipids using a dialysis bag (MWCO=10,000) for 2 days in water. A 200 nm syringe filter was used to remove any precipitation and the final concentration of the Fe and other metals in MLCCs was determined by ICP-MS analysis.

Drug Loading/Release

To prepare drug loaded MLCCs, first a stock solution by mixing equal volumes of DDAB (5-25 mg/ml) and drug (0.05-0.5 mg/ml) (CUR, PTX) solution in chloroform was prepared. The same procedure as MLCCs synthesis was repeated except instead of DDAB solution, the DDAB+drug stock solution was used. The final drug concentration was calculated using standard fluorescence plot of the drug. The drug encapsulation efficiency was calculated as (final drug concentration/initial drug concentration)*100. The amount of paclitaxel (PTX) entrapped within the MLCCs was measured by HPLC. For this, PTX loaded MLCCs were diluted with 5 times acetonitrile and sonicated in a water bath sonicator for 1 min for the drug to come out from the MLCCs and get dissolved in acetonitrile. Then the MLCCs were centrifuged for 10 min at 13,800 rpm at 10° C. Supernatants were taken out for the estimation of PTX entrapped by HPLC. 200 µl of samples were injected by autosampler and were analyzed with the mobile phase of acetonitrile: water (80:20 v/v), with a flow rate of 1 ml/min using Agilent HPLC-1100 system. Amount of paclitaxel was quantified by a diode array detector at 228 nm. The amount of drug (paclitaxel) in samples was determined from the peak area correlated with the standard curve.

Thermal activation/drug release experiments were performed on an MSI Automation Inc. Hyperthermia Research System RF generator at a frequency of 300 kHz and a power of 7 kW. A 0.2 mL suspension was placed inside the 5 cm coil generating the AC magnetic field of 5 kA/m. A non-magnetic nonmetallic optical temperature probe (Fiso) was used to monitor the temperature. Each experiment time duration was 20 minutes. Released drug was separated by centrifuge and the supernatant's fluorescence was measured to calculate amount of released drug.

Structural Characterization

Particle size and Energy Dispersive X-ray (EDX) was observed on a Hitachi H8100 TEM (200 kV) and Hitachi HD2300 (200 kV). The hydrodynamic diameter of the nanostructures was measured by Malvern Zeta Sizer Nano S-90 dynamic light scattering (DLS) instrument.

Measurement of $r_2$ Relaxivity

Samples (MLCCs, Citrate MNS, Ferumoxytol®) were diluted to concentrations ranging from 0.01 to 0.3 mM of metal ions. $T_2$ relaxation times were determined at 3.0 T Magnetom Verio (Siemens Healthcare, Erlangen, Germany) using the multiple-echo-fast-spin-echo sequence. Multiple echo Spin echo sequence with TR=1290 ms, 8 echo times starting with 9.9 to 79.2 ms, 160 mm FOV, 256×256 matrix, slice thickness 3 mm. Given that multiple samples had a distribution of T2 relaxation times, the range of echo times was limited. A commercial 12 channel head coil (diameter ~160 mm) was used. A 1.5 mL eppendorf centrifuge tube was used as a sample holder. $R_2$ maps were generated using a custom software using Matlab. The signal decay was fit to a single exponential function to estimate $T_2$ on a pixel by pixel basis.

Cell Culture

HepG2 liver cancer cell line and J774 murine macrophage cells (provided by Prof. Colby Shad Thaxton, Department of Urology, Feinberg School of Medicine, Northwestern University) were grown in RPMI-1640 medium containing 10% FBS and penicillin/streptomycin (100 units/mL and 100 µg/mL, respectively). The cells were cultured at 37° C. with 5% $CO_2$ atmosphere in T75 flasks.

MTS Assay for Cell Viability Test

The biocompatibility of the MLCCs and cytotoxicity was tested using MTS (3-(4,5-dimethylthiazol-2-yl)-5-(3-carboxymethoxyphenyl)-2-(4-sulfophenyl)-2H-tetrazolium) assay. Briefly, J774 and HepG2 cells were plated at $1\times10^5$ cells per well in 24-well plate with 70-80% of confluency. For biocompatibility study, J774 and HepG2 cells were incubated with MLCCs without drug at concentrations ranging from 9, 18, 45 µM Fe containing MLCCs/mL for 24 h at 37° C. For cytotoxicity study, HepG2 cells were incubated with MLCCs or drug loaded MLCCs at concentrations ranging from 9, 18, 45 µM Fe containing MLCCs/mL for 24 h at 37° C. To compare the effect of drug loaded MLCCs with native drug, Cells were also treated with different concentration of native drug (similar to amount of drug entrapped within the MLCCs as calculated from measurement via HPLC). After 24 h of treatment, cells were trypsinized, washed and only specified cells were exposed to thermal activation for 20 min and then again reseeded in the 24-well plate. The, after 24 h, cells were treated with MTS reagent for 2 h at 37° C. MTS assay was used to quantify the cell viability according to the protocol provided by the manufacture (CellTiter 96 Aqueous One Solution Cell Proliferation Assay; Promega). The optical densities were recorded at 490 nm and 700 nm using BioTek Synergy™ 4 Hybrid Microplate Reader. The background absorbance at 700 nm was subtracted from absorbance at 490 nm. The percentage of cell viability in different treatments were calculated in relation to the control samples (Cells without any treatment kept in same condition considered as 100% viable). The $IC_{50}$ values were calculated by nonlinear curve fit using dose response-inhibition equation with Graphpad Prism 5.0. The combination index was calculated using the following formula $$\text{Combination index}=[CI_1]/I_1+[CI_2]/I_2$$

Where $[CI_1]$: Concentration of therapy 1 in combined treatment to induce $IC_{50}$
$[CI_2]$: Concentration of therapy2 in combined treatment to induce $IC_{50}$
$[I_1]$: Concentration of therapy 1 to induce IC50 individually
$[I_2]$: Concentration of therapy 1 to induce IC50 individually Quantitative Analysis of Cellular Uptake Pattern HepG2 cells were plated at $4\times10^6$ cells per well in T25 flask with 70-80% of confluency one day prior to particle treatment. Then, the cells were cultured in various concentrations (0.9-36 µM Fe containing MLCCs/ml) for 24 hours. Untreated cells were used a control. Cells were washed with DPBS and then processed for ICP-MS to quantify the Fe quantity present in the cells. 2 µl from each sample was used to quantify the total protein content in each sample. For ICP-MS, cells were digested with 3% nitric acid overnight and next day processed for ICP-MS. (iCapQ ICP-MS, Billerica, Thermo Fischer Scientific,). The amount of Fe in cell samples were represented as µg Fe per µg protein sample.

Transmission Electron Microscopy of Cell Pellet

The cellular uptake was confirmed by TEM/EDS of the HepG2 cells ($4\times10^6$ cells in T25 flask) incubated with 1 µg Fe containing MLCCs/ml for 4 h. After incubation, cells were collected, fixed with 2.5% glutaraldehyde and 2% formaldehyde mixture. A post-fixation was done with osmium tetroxide. After dehydrating by a series of ethanol washes, the sample is embedded in resin. Ultramicrotome sections were placed on TEM grid and images were taken along with EDS analysis.

In Vitro MRI

HepG2 cells were plated at 4×10$^6$ cells in T25 flask with 70-80% of confluency one day prior to particle treatment. Cells were cultured in various concentrations (0.005, 0.1, 0.2, 0.3, 0.4 and 0.5 μg Fe containing MLCCs/ml) for 4 hours. Untreated cells were used a control. Cell pellets were collected and placed in capillaries and closed at both the ends. After arranged, the cell pellets were imaged using 7T Bruker Biospin MRI (Bruker Biospin, Billerica, Mass.). The images were processed using Paravision 6.0 software.

Results and Discussion

Figure 1:
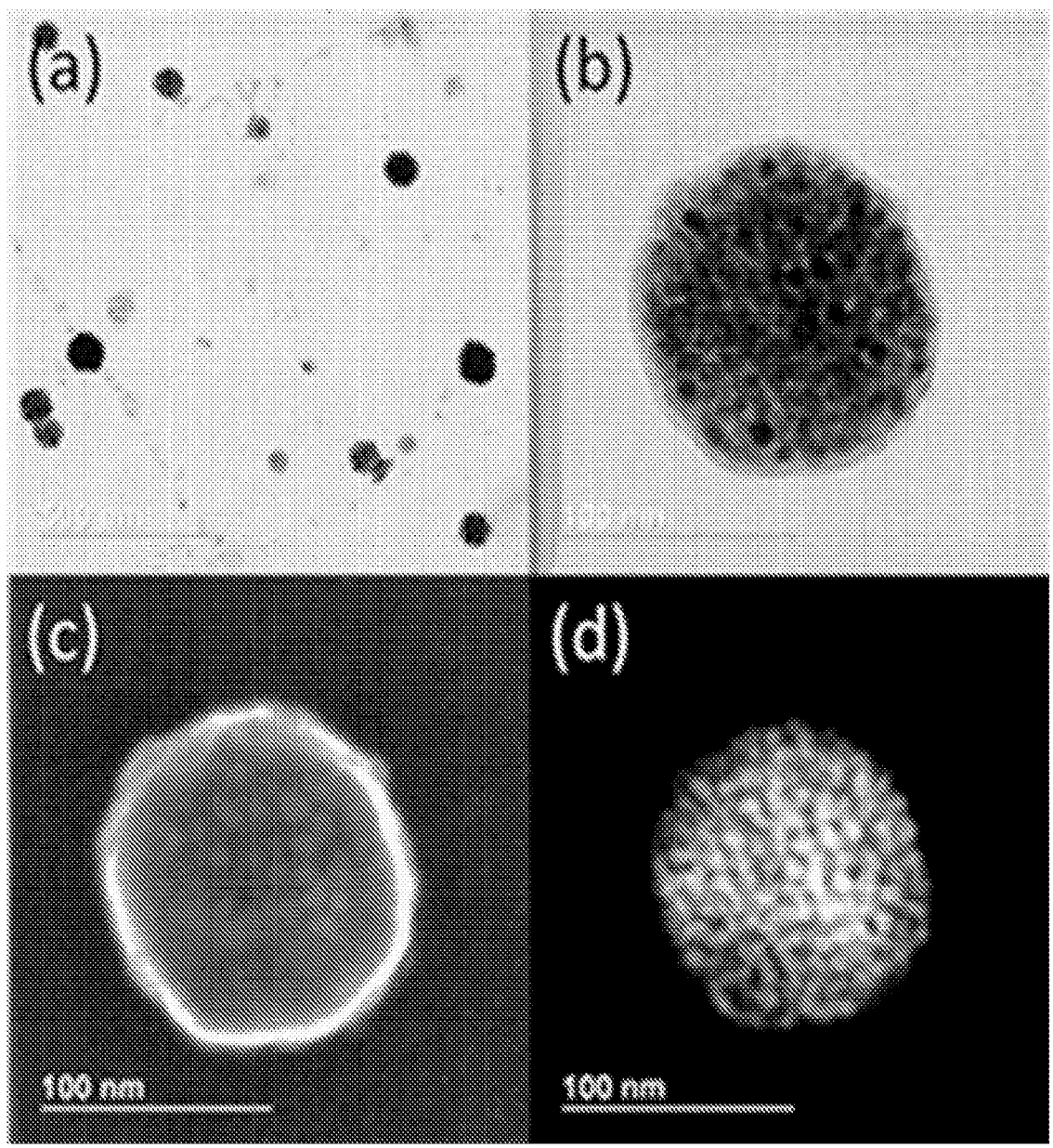
FIG. 1. (a,b) Bright field TEM and (d) dark field TEM of MNS-lipid composite carriers.
Figure 2:
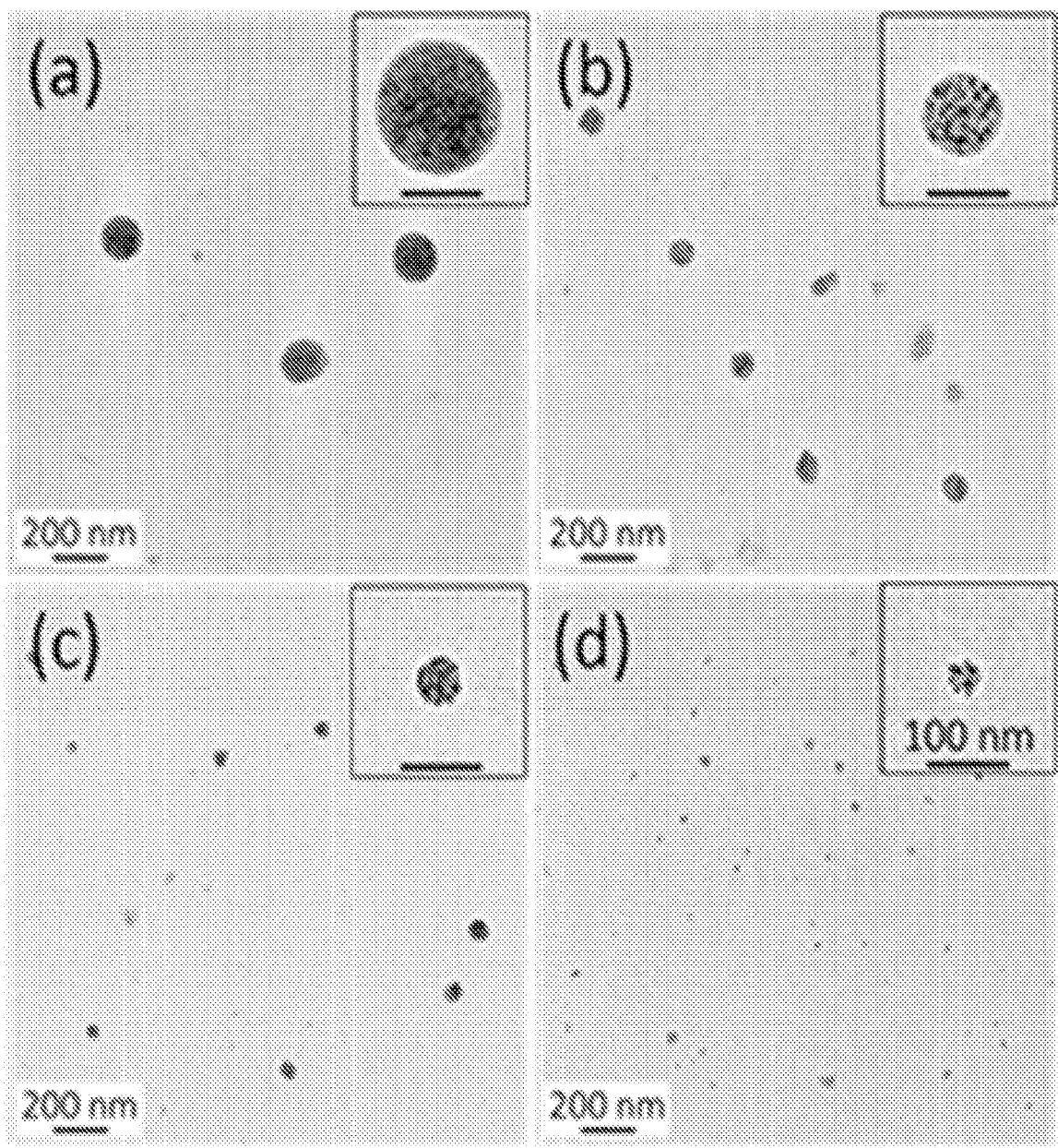
FIG. 2. TEM images of (a) 150 nm, (b) 100 nm, (c) 50 nm, and (d) 30 nm magnetic-lipid composite nanoparticles composed of 8 nm citrate MNS (inset scale bar 100 nm).
Figure 3:
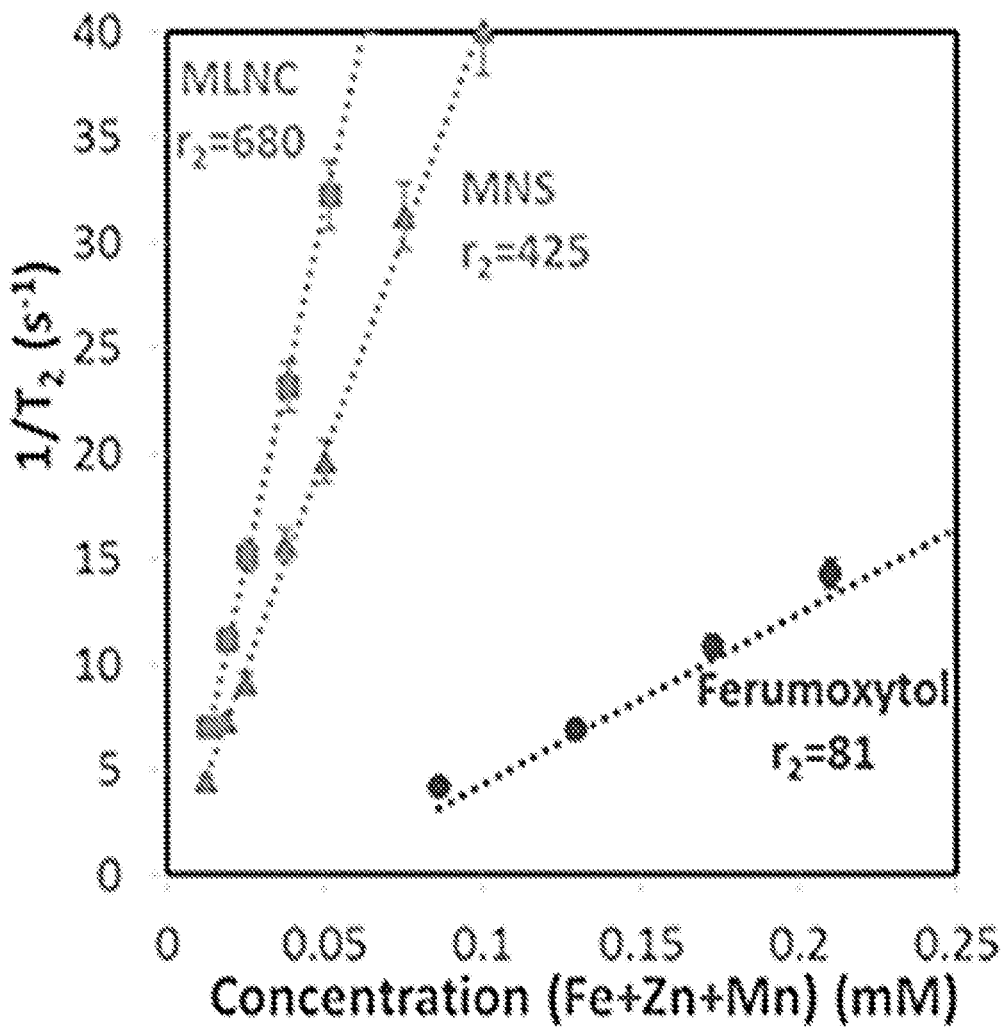
FIG. 3. r2 relaxivity plots and colored intensity maps of Ferumoxytol®, citrate MNS, and magnetic-lipid composite nanoparticles at 3T.
Figure 3:
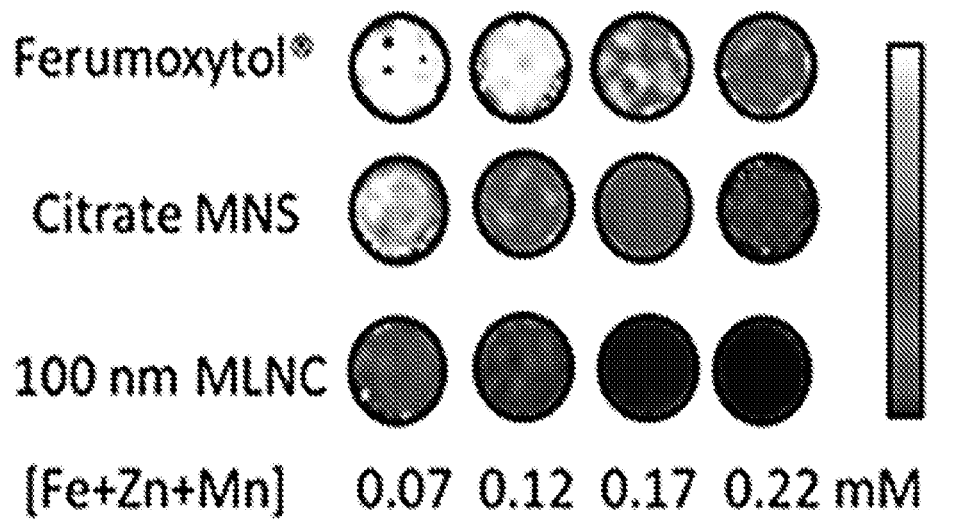

FIG. 1 shows TEM images of unstained MLCCs of size 100 nm where assembly of 8 nm citrate MNS and lipids on surface of NC can be seen in three different modes (bright field, dark field, scan mode). The TEM of a crumbled composite nanoparticle demonstrate their hollow core structure (ESI FIG. 1). The hydrodynamic size and zeta potential was observed as ~180 nm and ~28 mV. MLCC formation mechanism was validated when citrate MNS/neutral lipid (DPPC) or amine MNS/DDAB were mixed. No MLCC formation was observed due to the absence of complementary interactions (ESI FIG. 2). The size of the MLCCs were controlled by tuning lipid/MNS molar ratio. Magnetic-Lipid Composite nanoparticles of size 25 nm to 450 nm were synthesized using 8 nm MNS (FIG. 2). However, for all diagnostic and therapeutic experiments, 100 nm MLCCs composed of 8 nm citrate MNS were used due to their optimum size range and physical properties. Physical properties (saturation magnetization, $r_2$ relaxivity, and thermal activation) of MLCCs were size dependent.

Contrast Enhancement

MLCCs' use as an MRI $T_2$ contrast agent was investigated by measuring the spin-spin relaxation time ($T_2$) using magnetic resonance imaging (MRI) with field strength of 3 Tesla. During magnetic resonance imaging (MRI), magnetic field surrounding the MNS affect relaxation of water protons that are in proximity, resulting in increase in MR contrast (Ref 14; incorporated by reference in its entirety).The $T_2$ contrast enhancement effect is measured by r2 relaxivity, a slope of relaxation rate $R_2$ (s$^{-1}$) plotted against MNS metal concentration (mM). The higher relaxivity corresponds to higher $T_2$ contrast enhancement effect.

The $r_2$ relaxivity of MLCCs (680 mM$^{-1}$s$^{-1}$) was found much higher than citrate MNS (1.5 times) and Ferumoxytol® (8.5 times). This can be explained via the synergistic interactive magnetism theory reported by Gillis et. al (Ref 15; incorporated by reference in its entirety). Nanoclusters made of magnetic nanoparticles generate a stronger magnetic moment per unit volume than isolated magnetic nanoparticles. The stronger magnetic field surrounding clusters directly influences the water proton resonance (Ref 16; incorporated by reference in its entirety). The $r_2$ relaxation of magnetic nanoclusters have been shown as (Ref 15; incorporated by reference in its entirety):

$$r_2 = \left(\frac{64\pi}{135}\right)\left(\mu N_g \frac{L(x)}{4\pi}\right)^2 \frac{N_A C_a}{R_a D} \quad (1)$$

where μ is magnetic moment of the nanoparticle, $N_g$ is number of nanoparticles assembled in cluster, $C_a$ is concentration of cluster, $R_a$ is average radius of cluster, D is water diffusion coefficient, $N_A$ is Avogadro's number, and L(x) is Langevin function. According to the equation (1), $r_2$ is proportional to magnetic moment and number of Ng. Thus, incorporating MNS into MLCCs marginally improved their $r_2$ relaxivity and demonstrated MRI contrast enhancement 7 times higher than FDA-approved $T_2$ contrast agent Ferumoxytol®.

Drug Loading and Release

Figure 4:
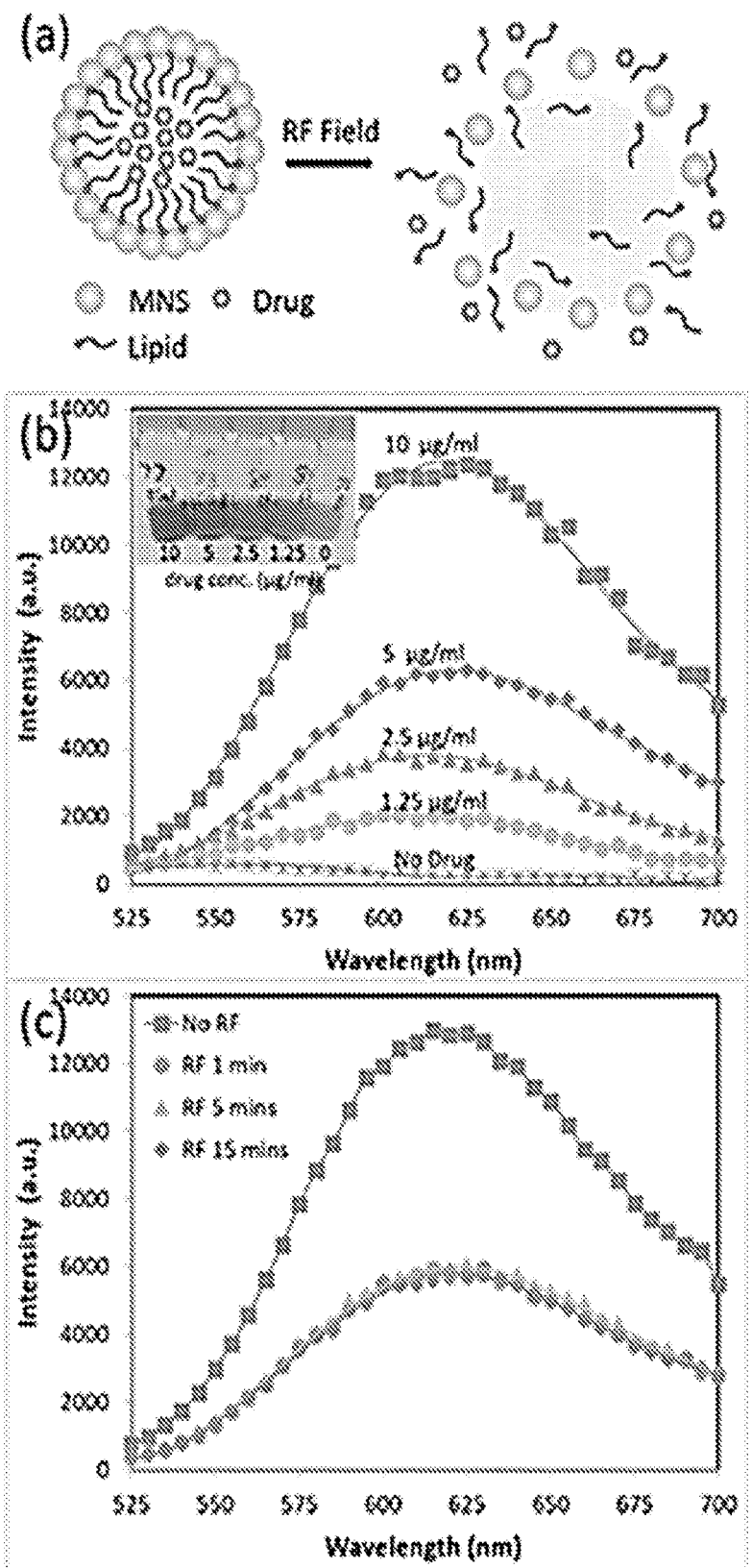
FIG. 4. (a) MNS-lipid composite carriers loaded with drug concentration ranging from 0 to 10 µg/ml (b) time-dependent drug release of MNS-lipid composite carriers under RF field (325 kHz, 6.3 kW) for 1,5, and 15 mins.

In order to validate MLCC as the drug delivery carrier, hydrophobic drug curcumin (CUR) was used as a model drug. Drug loading was achieved by mixing drug into lipid solution during MLCC formation. A systematic increase in fluorescent intensity from low to high CUR concentrations (0 to 10 μg/ml) demonstrates the success of the drug loading technique and unveils its potential to incorporate controlled amounts of drugs into the MLCCs (FIG. 4b). Nearly 80% of the drug was incorporated into the MLCCs. Both, sustained and actuated release were studied. For the actuated drug release study, MLCCs with 10 μg/ml of CUR was exposed to RF field (5 kA/m, 300 kHz) for 1, 5, and 15 mins. Thermal activation of MLCCs resulted in substantial amount of the CUR release as observed in drop of fluorescent intensity (FIG. 4b). Time did not affect the amount of drug release, indicating that release occurs as an actuation mechanism rather than diffusion mechanism. For sustained release study, fluorescence of CUR loaded MLCCs at different time intervals were measured. Figure shows that even after 14 days, ~50% of drug were still present which makes MLCC a very good nanocarrier for sustained release of lipophilic drugs. The drug release can be further be tuned by controlling the porosity of the MLCCs.

Cellular Viability and Uptake Studies

Figure 5:
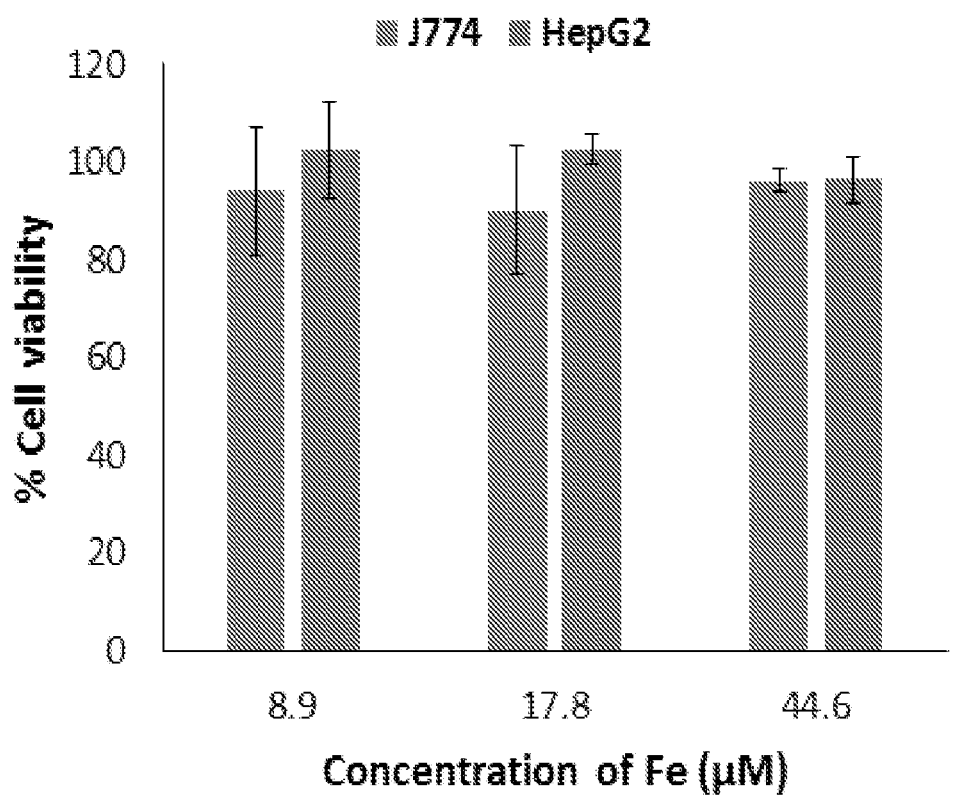
FIG. 5. Cell viability study using MTS assay. J774 murine macrophage cells and HepG2 cancer cells were treated with different concentrations of MNS-lipid composite carriers without and with thermal induction and 24 h post treatment the cell viability was assessed.

To investigate the in vitro use of the MLCCs, the biocompatibility of the MLCCs was tested in two different cell lines J774 and HepG2. With increasing concentration of MLCCs there was no significant difference in the percentage of cell viability in both the cell lines which suggests the biocompatibility of the capsule formulations (FIG. 5).

Figure 6:
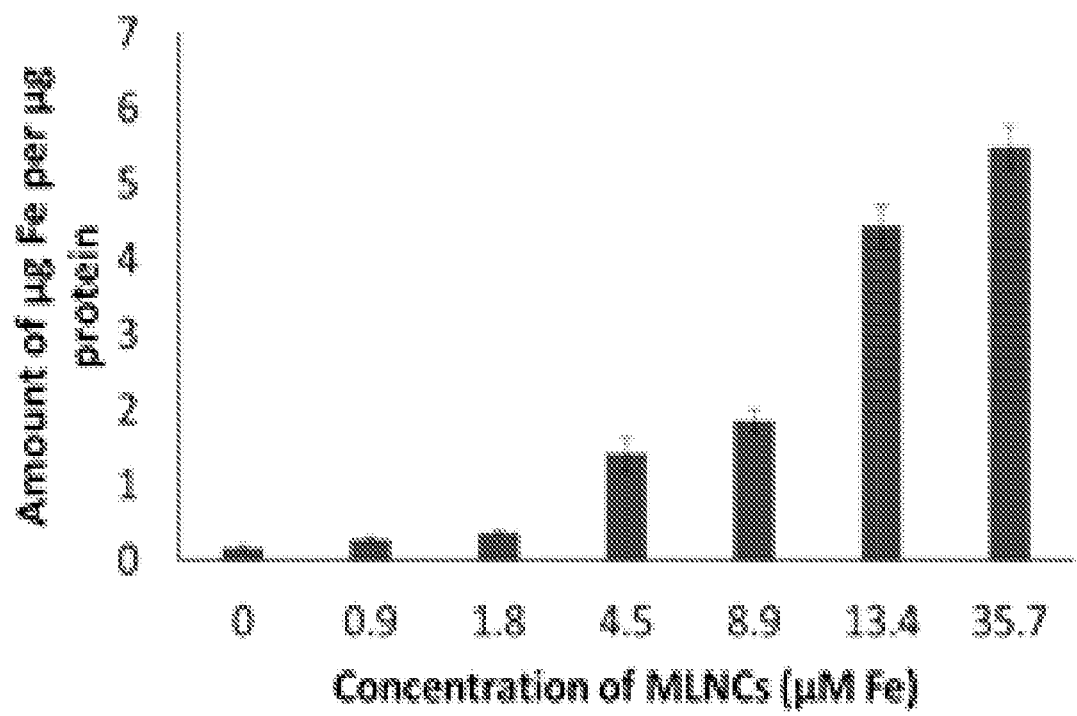
FIG. 6. The cellular uptake of MNS-lipid composite carriers was studied in HepG2 cancer cell line in a concentration dependent manner and measured using ICP-MS.
Figure 7:
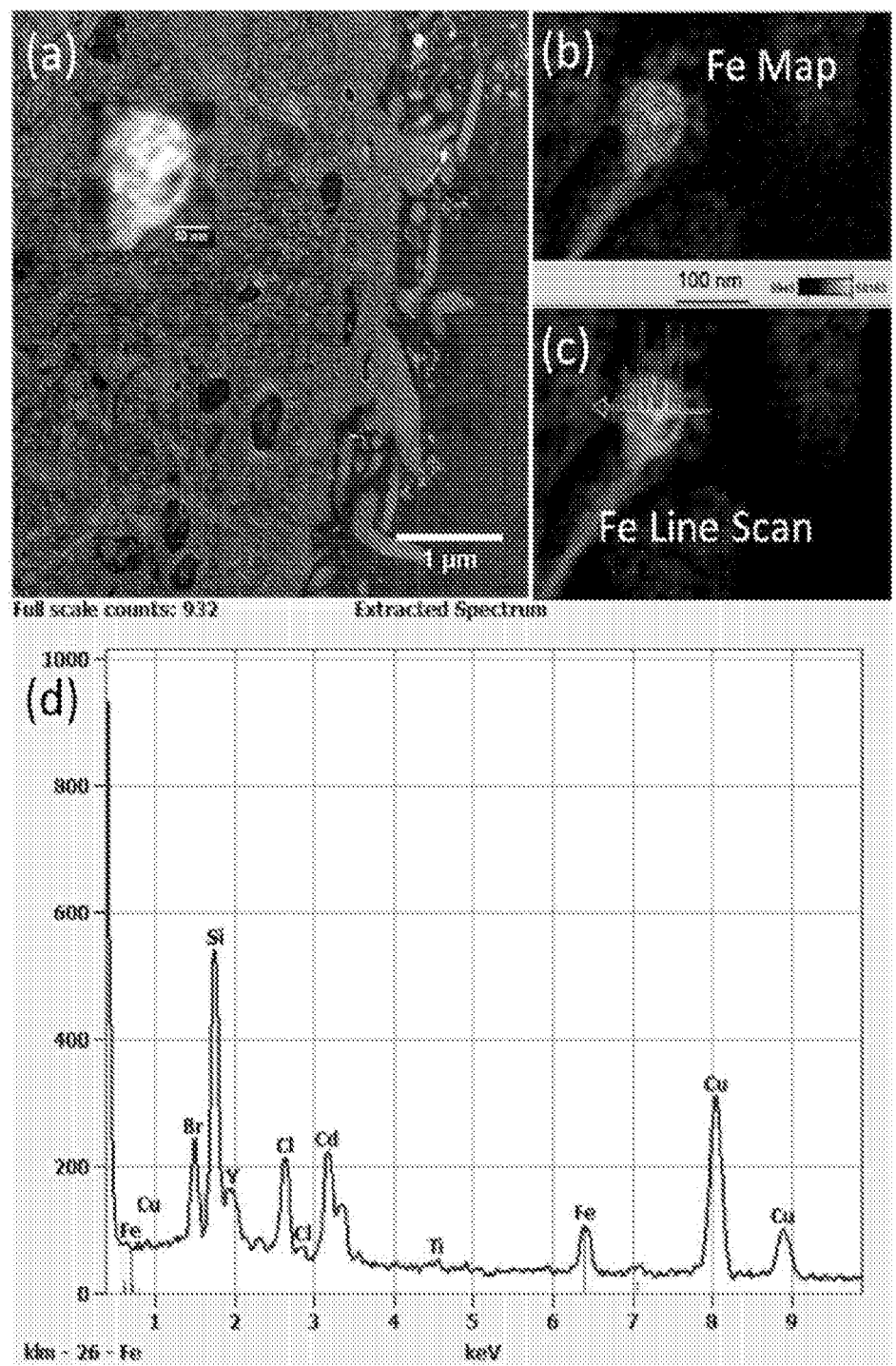
FIG. 7. TEM image and EDS (energy dispersive spectrum) of MNS-lipid composite carriers uptaken by HepG2 hepatic cancer cells.

The uptake study results indicated that there was an increase in the uptake of the MLCCs with increasing concentrations (FIG. 6). The TEM/EDS analysis confirmed the internalization of MLCCs by the HepG2 cells. The structure of the MLCCs were found to be maintained in the cells. EDS spectral and point scans show the presence of iron confirming the presence of particles inside cells (FIG. 7).

Figure 8:
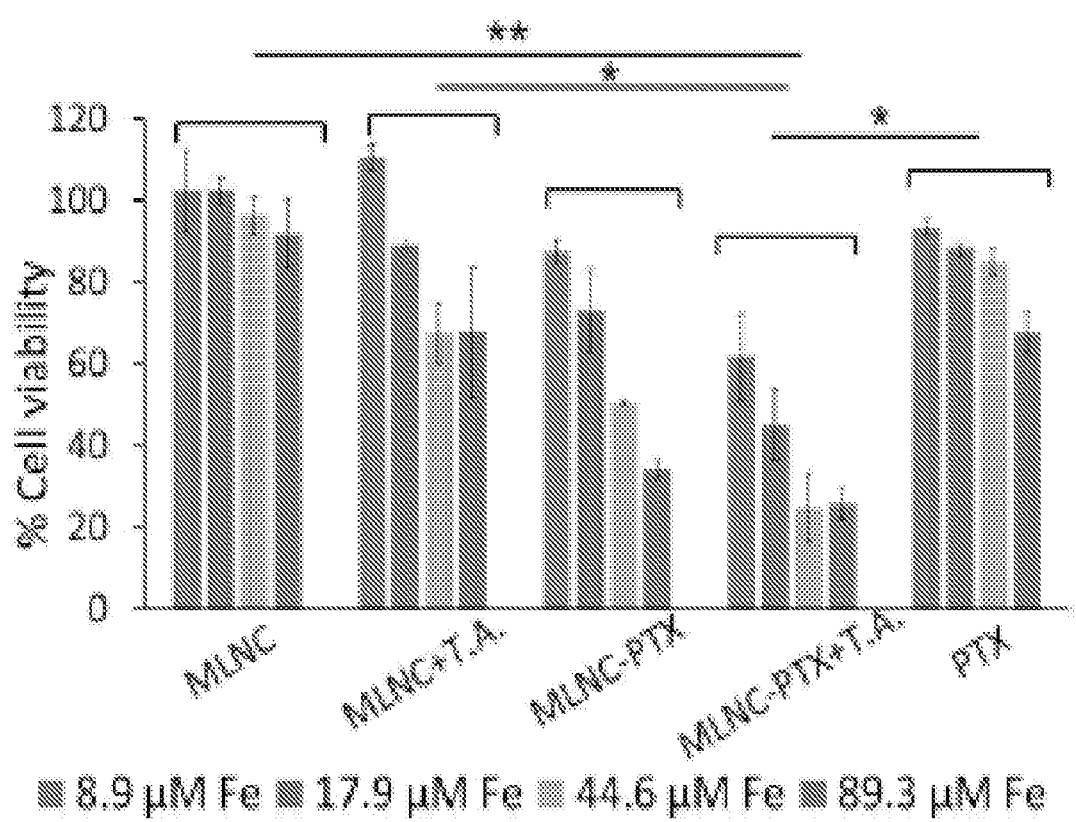
FIG. 8. Cell viability study using MTS assay. HepG2 cancer cells were treated with different concentrations of capsules and drug loaded capsules without and with thermal induction and 24 h post treatment the cell viability was assessed. **$p<0.001$, *$p<0.05$ Combinationa therapy vs single treatments. Significance calculation done by One-way anova using GraphPad prism 5.0.

As demonstrated above, drugs loaded into MLCCs can be released in a controlled manner via thermal activation of MLCCs under RF field. To demonstrate therapeutic effect, a potent anticancer drug paclitaxel (PTX) has been loaded into MLCCs. The amount of PTX in the MLCCs was calculated by HPLC. The HPLC results indicated that 1 μg of PTX was entrapped within 357.2 μM Fe containing MLCCs. Different concentrations of MLCCs with and without PTX were incubated with HepG2 cells and exposed to RF field for 15 mins. FIG. 8 presents in vitro cytotoxicity effects of drug loaded MLCCs. The MLCCs without drug exhibited was biocompatible with HepG2 cells. The reduction in cell viability was observed when PTX loaded MLCCs were treated with HepG2 cells (MLCCs+PTX), indicating PTX induced cytotoxicity in HepG2 cells. The cytotoxicity effect induced by PTX loaded MLCCs were found to be higher than that of free PTX. This suggests the enhanced therapeutic efficacy of PTX loaded MLCCs as compare to free PTX. The $IC_{50}$ values in HepG2 cells for native PTX and PTX loaded capsules were calculated to be 0.63 and 0.13 μg PTX/ml respectively which suggests 5 times enhancement of drug efficiency after encapsulation within the composite nanoparticles. It has been previously reported when treated with cancer cells, the free drugs are less cytotoxic compares to the drugs loaded into nanocarriers due to membrane efflux pumps and the multi-drug resistance (MDR) that pushes out free drugs from cytosol to extra cellular area, reducing their efficacy.[17] The cytotoxicity effect of PTX loaded MLCCs was also found to increase in a dose dependent manner (FIG. 8).

TABLE 1

$IC_{50}$ values of different treatments of MLCCs in HepG2 cells after 48 h, calculated using GraphPad Prism 5.0.

| Sample | $IC_{50}$ µM Fe containing capsule | $IC_{50}$ µg PTX/ml |
|---|---|---|
| Capsule | — | — |
| Capsule + T.A. | 139.9 | — |
| Capsule − PTX | 46.8 | 0.13 |
| Capsule − PTX + T.A. | 14.64 | 0.04 |
| PTX | — | 0.63 |

Cells treated with MLCCs without drug and exposed to thermal activation also induced toxicity in the HepG2 cancer cells. However, the combination of PTX loaded capsules and thermal activation showed the maximum cytotoxicity in HepG2 cells with cell death up to 80%. The $IC_{50}$ value of PTX-capsules with thermal activation was reduced to 0.04 µg PTX/ml.

To check whether the effect of combination therapy is additive or synergistic, combination index was calculated. The CI was found to be 0.163 which shows both kind of therapies to be highly synergistic in combination. Such an increased cytotoxicity in combination therapy can be attributed to different reasons. First, thermal activation of MNS via RF field helps in burst release of encapsulated drugs by inducing structural instability to the MLCCs. Such application of RF to release encapsulated drug has been demonstrated previously on MNS based hydrogel platform.[18] The second probable reason of enhanced cytotoxicity is the increase in sensitivity of the cancer cells towards anticancer drugs after exposure to thermal therapy.[19] In different other experimental setups, it has been seen that thermal activation helps to increase the effectiveness of radiotherapy or chemotherapy, that has been clinically tested in different cancer patients including malignant melanoma, glioblastoma, cervical cancer, and lymph node metastases.[20]

Figure 9:
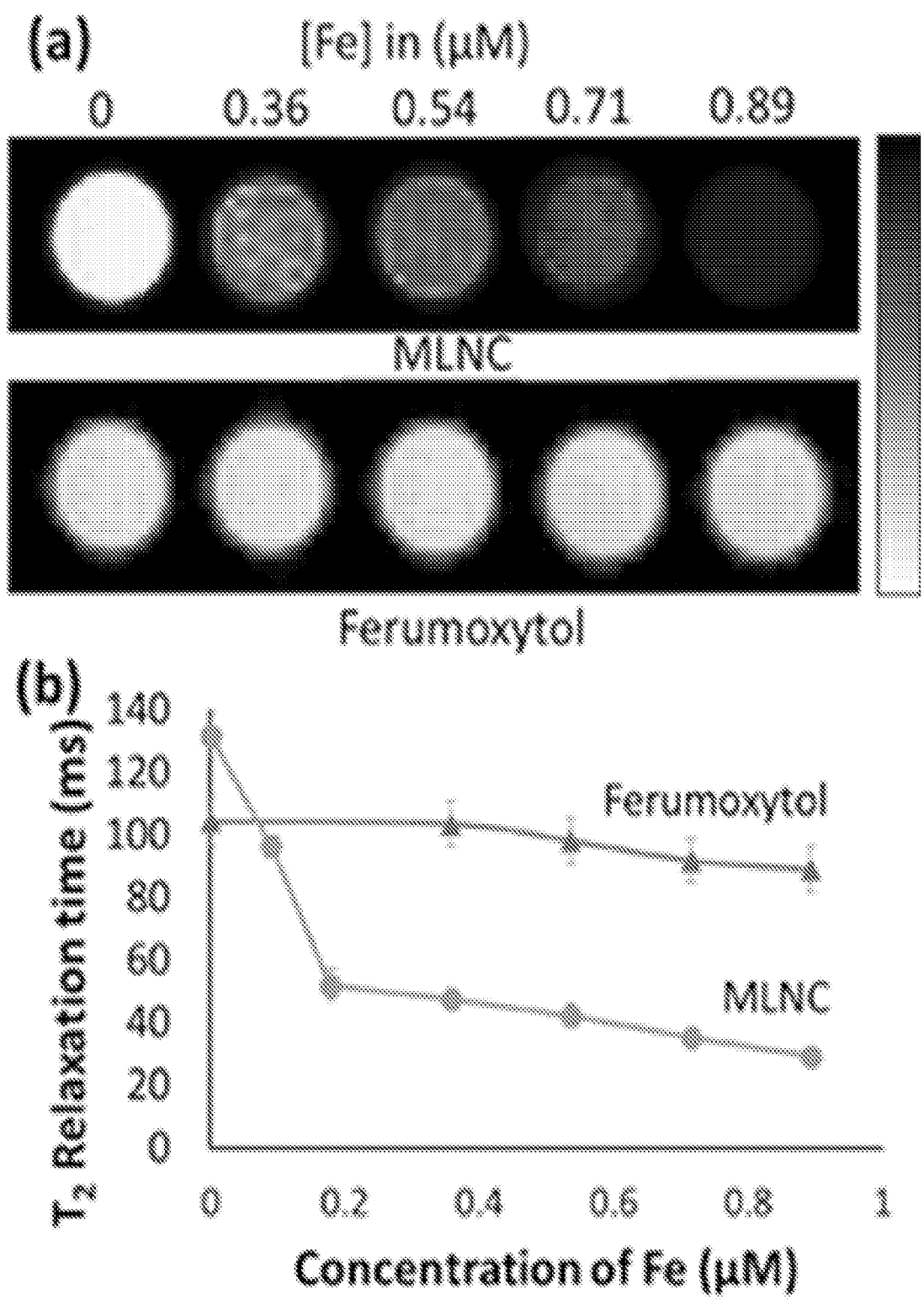
FIG. 9. (a) Magnetic resonance imaging (MRI) of HepG2 cell pellets treated with different concentrations of MNS-lipid composite carriers using 7T Bruker Biospin MRI. (b)

In Vitro MRI $T_2$-weighted MR images of MLCCs were taken in HepG2 cells after incubating the cells with different concentrations of MLCCs for 4 h (FIG. 9). $T_2$-weighted MR phantom images show a darker signal (decrease in $T_2$ relaxation time) with the increase of MLCC concentration. The relaxation time drop even at very low concentration of MLCCs as compared to Ferumoxytol® demonstrate the higher contrast enhancement properties of MLCCs.

Versatile Platform

Since the synthesis of the composite nanoparticles is based on complementary functionalities, the assembly formation was extended to other nanoparticles and lipids of different types/sizes, resulting in composite nanoparticles with distinct physical properties. FIG. 10 shows TEM and EDX of magnetic, plasmonic, and semiconducting composite nanoparticles of different sizes assembled from 4 nm and 8 nm $Fe_3O_4$ NPs, 13 nm Au NPs, and 6 nm ZnS QDs, respectively. Instead of DDAB, DOTAP (1,2-dioleoyl-3-trimethylammonium-propane) as cationic lipid also resulted in formation of composite nanoparticle (data not shown). Experiments also demonstrate that the synthetic method can be used to fabricate hybrid structures using combination of nanoparticles. MLCC with only 18 nm (FIG. 11b) and 18 and 8 nm MNS were prepared. Assembly of NPs results in collective physical properties,[21] therefore physical properties of composite nanoparticles can be further tuned by tuning their size. Due to its simple and versatile nature, this synthetic method can be used to fabricate multifunctional hybrid structures using combination of nanoparticles encapsulated and/or embedded in the lipid layer with tunable physical properties (FIG. 11a).

FIGS. 13 and 14 show TEM of collapsed MLCC and control experiments.

Example 2

Cisplatin (CPT) is a well-known hydrophobic anti-cancer drug. Experiments conducted during development of embodiments herein have demonstrated that MLCCs are useful for targeted delivery of cisplatin (CPT). FIG. 15 shows cytotoxicity study of HepG2 cancer cells when treated with different concentrations of MLCCs with CPT and corresponding controls under the application of RF field. All the experimental conditions (drug lipid ratio, drug MNS ratio, cell culture conditions) are same as used for PTX.

REFERENCES

The following references, some of which are cited above by number, are herein incorporated by reference in their entireties.

[1] a) G. Y. Chen, I. Roy, C. H. Yang, P. N. Prasad, Chem Rev 2016, 116, 2826; b) Y. Z. Min, J. M. Caster, M. J. Eblan, A. Z. Wang, Chem Rev 2015, 115, 11147.
[2] S. Kunjachan, J. Ehling, G. Storm, F. Kiessling, T. Lammers, Chem Rev 2015, 115, 10907.
[3] a) D. Yoo, J. H. Lee, T. H. Shin, J. Cheon, Accounts Chem Res 2011, 44, 863; b) J. Kim, Y. Piao, T. Hyeon, Chem Soc Rev 2009, 38, 372; c) N. Lee, T. Hyeon, Chem Soc Rev 2012, 41, 2575; d) N. Lee, D. Yoo, D. Ling, M. H. Cho, T. Hyeon, J. Cheon, Chem Rev 2015, 115, 10637; e) L. H. Reddy, J. L. Arias, J. Nicolas, P. Couvreur, Chem Rev 2012, 112, 5818.
[4] a) V. Nandwana, M. De, S. Chu, M. Jaiswal, M. Rotz, T. J. Meade, V. P. Dravid, in Cancer treatment and research, Vol. volume 166 (Eds: C. A. Mirkin, T. J. Meade, S. Hurst Petrosko, A. H. Stegh), 2015, 51; b) V. Nandwana, S. R. Ryoo, S. Kanthala, M. De, S. S. Chou, P. V. Prasad, V. P. Dravid, Acs Appl Mater Inter 2016, 8, 6953; c) M. De, S. S. Chou, H. M. Joshi, V. P. Dravid, Adv Drug Deliver Rev 2011, 63, 1282; d) K. E. Sapsford, W. R. Algar, L. Berti, K. B. Gemmill, B. J. Casey, E. Oh, M. H. Stewart, I. L. Medintz, Chem Rev 2013, 113, 1904.
[5] a) D. Peer, J. M. Karp, S. Hong, O. C. FaroKHzad, R. Margalit, R. Langer, Nat Nanotechnol 2007, 2, 751; b) M. Mahmoudi, H. Hofmann, B. Rothen-Rutishauser, A. Petri-Fink, Chem Rev 2012, 112, 2323; c) H. Arami, A. Khandhar, D. Liggitt, K. M. Krishnan, Chem Soc Rev 2015, 44, 8576.
[6] a) K. Ulbrich, K. Hola, V. Subr, A. Bakandritsos, J. Tucek, R. Zboril, Chem Rev 2016, 116, 5338; b) J. Thevenot, H. Oliveira, O. Sandre, S. Lecommandoux, Chem Soc Rev 2013, 42, 7099; c) M. Molina, M. Asadian-Birjand, J. Balach, J. Bergueiro, E. Miceli, M. Calderon, Chem Soc Rev 2015, 44, 6161; d) M. Karimi, A.

Ghasemi, P. S. Zangabad, R. Rahighi, S. M. M. Basri, H. Mirshekari, M. Amiri, Z. S. Pishabad, A. Aslani, M. Bozorgomid, D. Ghosh, A. Beyzavi, A. Vaseghi, A. R. Aref, L. Haghani, S. Bahrami, M. R. Hamblin, Chem Soc Rev 2016, 45, 1457; e) C. Caltagirone, A. Bettoschi, A. Garau, R. Montis, Chem Soc Rev 2015, 44, 4645; f) J. L. Vivero-Escoto, R. C. Huxford-Phillips, W. B. Lin, Chem Soc Rev 2012, 41, 2673; g) Y. Wang, H. C. Gu, Adv Mater 2015, 27, 576.
[7] a) B. Fonseca-Santos, M. P. D. Gremiao, M. Chorilli, Int J Nanomed 2015, 10; b) D. K. Thukral, S. Dumoga, A. K. Mishra, Curr Drug Deliv 2014, 11, 771; c) M. Nasr, S. Abdel-Hamid, Curr Pharm Biotechno 2015, 16, 322.
[8] S. V. Talluri, G. Kuppusamy, V. V. S. R. Karri, S. Tummala, S. V. Madhunapantula, Drug Deliv 2016, 23, 1291.
[9] T. M. Allen, P. R. Cullis, Adv Drug Deliver Rev 2013, 65, 36.
[10] S. Mura, D. T. Bui, P. Couvreur, J. Nicolas, J Control Release 2015, 208, 25.
[11] a) H. Fattahi, S. Laurent, F. J. Liu, N. Arsalani, L. V. Elst, R. N. Muller, Nanomedicine-Uk 2011, 6, 529; b) W. J. M. Mulder, G. J. Strijkers, G. A. F. van Tilborg, A. W. Griffioen, K. Nicolay, Nmr Biomed 2006, 19, 142; c) B. Gamier, S. Tan, S. Miraux, E. Bled, A. R. Brisson, Contrast Media Mol I 2012, 7, 231; d) S. J. Soenen, G. Vande Velde, A. Ketkar-Atre, U. Himmelreich, M. De Cuyper, Wires Nanomed Nanobi 2011, 3, 197; e) S. J. H. Soenen, M. Hodenius, M. De Cuyper, Nanomedicine-Uk 2009, 4, 177; f) A. Floris, A. Ardu, A. Musinu, G. Piccaluga, A. M. Fadda, C. Sinico, C. Cannas, Soft Matter 2011, 7, 6239.
[12] L. F. Zhang, S. Granick, Nano Lett 2006, 6, 694.
[13] V. Nandwana, K. E. Elkins, N. Poudyal, G. S. Chaubey, K. Yano, J. P. Liu, J Phys Chem C 2007, 111, 4185.
[14] S. H. Koenig, K. E. Kellar, Magnet Reson Med 1995, 34, 227.
[15] A. Roch, Y. Gossuin, R. N. Muller, P. Gillis, J Magn Magn Mater 2005, 293, 532.
[16] a) S. Laurent, D. Forge, M. Port, A. Roch, C. Robic, L. V. Elst, R. N. Muller, Chem Rev 2008, 108, 2064; b) K. C. Barick, M. Aslam, P. V. Prasad, V. P. Dravid, D. Bahadur, J Magn Magn Mater 2009, 321, 1529.
[17] F. M. Kievit, F. Y. Wang, C. Fang, H. Mok, K. Wang, J. R. Silber, R. G. Ellenbogen, M. Q. Zhang, J Control Release 2011, 152, 76.
[18] M. K. Jaiswal, M. De, S. S. Chou, S. Vasavada, R. Bleher, P. V. Prasad, D. Bahadur, V. P. Dravid, Acs Appl Mater Inter 2014, 6, 6237.
[19] S. Purushotham, R. V. Ramanujan, Acta Biomater 2010, 6, 502.
[20] a) E. L. Jones, J. R. Oleson, L. R. Prosnitz, T. V. Samulski, Z. Vujaskovic, D. H. Yu, L. L. Sanders, M. W. Dewhirst, J Clin Oncol 2005, 23, 3079; b) P. Wust, U. Gneveckow, M. Johannsen, D. Bohmer, T. Henkel, F. Kahmann, J. Sehouli, R. Felix, J. Ricke, A. Jordan, Int J Hyperther 2006, 22, 673.
[21] a) M. A. Boles, M. Engel, D. V. Talapin, Chem Rev 2016, 116, 11220; b) S. Gwo, H. Y. Chen, M. H. Lin, L. Y. Sun, X. Q. Li, Chem Soc Rev 2016, 45, 5672; c) Z. D. Lu, Y. D. Yin, Chem Soc Rev 2012, 41, 6874.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. A nanoparticle-lipid composite carrier, consisting of:
   (a) a hydrophobic core consisting of tails of a plurality of lipid molecules, and optionally, an active agent encapsulated in the hydrophobic core, wherein the plurality of lipid molecules is in the form of a monolayer of lipid molecules such that the nanoparticle-lipid composite carrier does not comprise a bilayer of lipid molecules; and
   (b) a shell consisting of surface-functionalized nanostructures assembled on heads of the plurality of lipid molecules, wherein the nanostructures are magnetic nanostructures.

2. The nanoparticle-lipid composite carrier of claim 1, wherein said nanostructures are surface-functionalized with a negatively charged moiety.

3. The nanoparticle-lipid composite carrier of claim 2, wherein said negatively charged moiety is citrate.

4. The nanoparticle-lipid composite carrier of claim 1, wherein the plurality of lipid molecules consist of a cationic lipid, or an amphiphilic surfactant with a cationic head group.

5. The nanoparticle-lipid composite carrier of claim 4, wherein the plurality of lipid molecules consist of dimethyl dioctadecyl ammonium bromide (DDAB) or 1,2-dioleoyl-3-trimethylammonium-propane (DOTAP).

6. The nanoparticle-lipid composite carrier of claim 1, wherein the hydrophobic core encapsulates the active agent.

7. The nanoparticle-lipid composite carrier of claim 6, wherein said active agent is a drug.

8. The nanoparticle-lipid composite carrier of claim 7, wherein said drug is a chemotherapeutic agent.

9. The nanoparticle-lipid composite carrier of claim 1, wherein said magnetic nanostructures have a diameter of 2-20 nm.

10. The nanoparticle-lipid composite carrier of claim 9, wherein said magnetic nanostructures have at least two different sizes.

11. A method, comprising
   a) administering the nanoparticle-lipid composite carrier of claim 1 to a cell; and
   b) destroying said cell by exposing said nanoparticle-lipid composite carrier to a radio frequency that causes said nanoparticle-lipid composite carrier to generate heat.

12. The method of claim 11, wherein said cell is a cancer cell.

13. A method, comprising
   a) administering the nanoparticle-lipid composite carrier of claim 1 to a cell, wherein the hydrophobic core encapsulates the active agent and the active agent is a drug; and
   b) releasing said drug.

14. The method of claim 13, wherein said drug is released via exposure to radio frequency.

15. The method of claim 11, further comprising the step of imaging said nanoparticle-lipid composite carrier using MRI.

16. A method, comprising:
   a) contacting a cell with the nanoparticle-lipid composite carrier of claim 1; and b) imaging said nanoparticle-lipid composite carrier using MRI.

17. A method of synthesizing the nanoparticle-lipid composite carrier of claim 1, the method comprising:
contacting lipid molecules with surface-functionalized nanostructures under conditions such that the nanoparticle-lipid composite carrier consisting of the hydrophobic core consisting of tails of the plurality of the lipid molecules and optionally, the active agent encapsulated in the hydrophobic core, and the shell consisting of the surface-functionalized nanostructures assembled on heads of the plurality of the lipid molecules is self-assembled, wherein the plurality of the lipid molecules is in the form of the monolayer of the lipid molecules such that the nanoparticle-lipid composite carrier does not comprise the bilayer of the lipid molecules, and wherein the nanostructures are magnetic nanostructures.

18. The nanoparticle-lipid composite carrier of claim 1, wherein said nanostructures are surface-functionalized with a negatively charged moiety and wherein the plurality of lipid molecules consist of a cationic lipid, or an amphiphilic surfactant with a cationic head group.

* * * * *